US 6,403,097 B1

(12) United States Patent
Rijsewijk et al.

(10) Patent No.: US 6,403,097 B1
(45) Date of Patent: *Jun. 11, 2002

(54) BOVINE HERPESVIRUS TYPE 1 DELETION MUTANTS, VACCINES BASED THEREON, DIAGNOSTIC KITS FOR DETECTION OF BOVINE HERPESVIRUS TYPE 1

(75) Inventors: Franciscus Antonius Maria Rijsewijk, Amsterdam; Johannes Theodorus van Oirschot, Lelystad, both of (NL)

(73) Assignee: Stichting Centraal Diergeneeskundig Instituut, Lelystad (NL)

( * ) Notice: Subject to any disclaimer, the term of this patent is extended or adjusted under 35 U.S.C. 154(b) by 0 days.

This patent is subject to a terminal disclaimer.

(21) Appl. No.: 08/949,788

(22) Filed: Oct. 14, 1997

Related U.S. Application Data

(63) Continuation of application No. 08/150,203, filed as application No. PCT/NL92/00097 on Jun. 5, 1992, now Pat. No. 5,676,951.

(30) Foreign Application Priority Data

Jun. 7, 1991 (NL) .............................................. 9100989

(51) Int. Cl.[7] .................... A61K 39/245; A61K 39/265; C12N 7/01; C12N 15/83
(52) U.S. Cl. ................................. 424/199.1; 424/205.1; 424/229.1; 435/235.1; 435/320.1; 435/236
(58) Field of Search ........................ 435/6, 5, 7.1, 7.92, 435/7.93, 7.94, 235.1, 320.1, 236; 424/199.1, 204.1, 229.1, 205.1

(56) References Cited

U.S. PATENT DOCUMENTS 4,992,051 A * 2/1991 Kit et al. .................. 435/235.1
5,599,544 A * 2/1997 Cochran et al. .......... 424/229.1

5,676,951 A * 10/1997 Rijsewijk et al. ........ 424/229.1

FOREIGN PATENT DOCUMENTS

| EP | 0316658 | * | 5/1989 |
| EP | 0326127 | * | 8/1989 |
| WO | 89/910965 | * | 11/1989 |

OTHER PUBLICATIONS

Lugovic et al. Veterinarski Arhiv 55, 241–245, 1985.*

Dekkers, et al., "Agricultural Biotechnology in Focus in the Netherlands", Pudoc Wageningen, vol. —, pp. 122–127, (1990).*

H. Neidhardt et al –Herpes Simplex Virus Type 1 Glycoprotein E Is Not Indispensable for ViralInfectivity, J. of Virol., vol. 61, No. 2, Feb. 1, 1987, pp. 600–603.*

S. Chatterjee et al –A Role for Herpes Simplex Virus Type 1 Glycoprotein E in Induction of Cell Fusion, J. Gen. Virol. (1989), vol. 70, pp. 2157–2162.*

Leung–Tack et al, Virology 199:409–421.*

* cited by examiner

*Primary Examiner*—Mary E. Mosher
(74) *Attorney, Agent, or Firm*—Hoffman & Baron, LLP

(57) ABSTRACT

A deletion mutant of bovine herpesvirus type 1 which has a deletion in the glycoprotein gE-gene and which may further have a deletion in the thymidine kinase gene and/or the glycoprotein gI-gene, or have an insertion of a heterologous gene is disclosed. Recombinant nucleic acids which encode the gE-gene or a part thereof are also disclosed, in addition to vaccines and a method of treatment.

13 Claims, 34 Drawing Sheets

FIG. 3A-1

```
AGGGCGGAGC GTTGAGCGGC CCGACCGCCG CCGGGTTGTT AAATGGGTCT CGGCGGCTC           60
                                  |----> deleted in Difivac1
GTGGTTCCAC ACCGCCGGAG AACCAGGCGCG AGCTTCGCTG CGTGTGTCCC GCGAGCTGCG        120
                                 AsuII
TTCCGGGGAA CGGCGCACGC GAGAGGGTTC GAAAAGGGCA TTTGGCA                       167

ATG CAA CCC ACC GCG CCG CCC CGG CGG TTG CTG CCG CTG CTG CTG               215
Met Gln Pro Thr Ala Pro Pro Arg Arg Leu Leu Pro Leu Leu Leu
 1               5                      10                  15
====================== SIGNAL PEPTIDE ==================

CCG CAG TTA TTG CTT TTC GGG CTG ATG GCC GAG GCC AAG CCC GCG ACC           263
Pro Gln Leu Leu Phe Gly Leu Met Ala Glu Ala Lys Pro Ala Thr
                 20                      25                  30
==================================================

SmaI
GAA ACC CCG GGC TCG GCT TCG GTC GAC ACG GTC TTC ACG GCG CGC GCT           311
Glu Thr Pro Gly Ser Ala Ser Val Asp Thr Val Phe Thr Ala Arg Ala
         35                      40                      45

GGC GCG CCC GTC TTT CTC CCA GGG CCC GCG CGC GAC GTG CGC                   359
Gly Ala Pro Val Phe Leu Pro Gly Pro Ala Arg Pro Asp Val Arg
         50                      55                      60

GCC GTT CGC GGC TGG AGC GTC CTC GCG GGC GCC TGC TCG CCG GTG               407
Ala Val Arg Gly Trp Ser Val Leu Ala Gly Ala Cys Ser Pro Val
 65                      70                      75          80
```

FIG. 3A-2

```
CCG GAG CCC GTC TGC CTC GAC GAC CGC GAG TGC TTC ACC GAC GTG GCC    455
Pro Glu Pro Val Cys Leu Asp Asp Arg Glu Cys Phe Thr Asp Val Ala
            85                      90                      95

CTG GAC GCG GCC TGC CTG CGA ACC GCC CGC GTG GCC CCG CTG GCC ATC    503
Leu Asp Ala Ala Cys Leu Arg Thr Ala Arg Val Ala Pro Leu Ala Ile
            100                     105                     110

GCG GAG CTC GCC GAG CCC GAC TCA ACG GGC GAC AAA GAG TTT GTT        551
Ala Glu Leu Ala Glu Arg Pro Asp Ser Thr Gly Asp Lys Glu Phe Val
            115                     120                     125

PvuII
CTC GCC GAC CCG CAC GTC TCG GCG CAG CTG GGT CGC AAC GCG ACC GGG    599
Leu Ala Asp Pro His Val Ser Ala Gln Leu Gly Arg Asn Ala Thr Gly
            130                     135                     140

GTG CTG ATC GCG GCC GCA GCC GAG GAC GGC GGC GTG TAC TTC CTG        647
Val Leu Ile Ala Ala Ala Glu Asp Gly Gly Val Tyr Phe Leu
            145                     150                     155                     160

TAC GAC CGG CTC ATC GGC GAC GCC GGC GCA GAG ACG CAG TTG GCG        695
Tyr Asp Arg Leu Ile Gly Asp Ala Gly Ala Glu Thr Gln Leu Ala
            165                     170                     175

CTG ACG CTG CAG GTC GCG ACG GCC GGC CAG GGC GCC GCG CGG GAC        743
Leu Thr Leu Gln Val Ala Thr Ala Gly Gln Gly Ala Ala Arg Asp
            180                     185                     190
```

FIG. 3A-3

```
GAG GAG AGG GAA CCA GCG ACC GGG CCC ACC GGC CCC CCG CCC CAC         791
Glu Glu Arg Glu Pro Ala Thr Gly Pro Thr Gly Pro Pro Pro His
            195                 200                 205

CGC ACG ACA CGC GCG CCC CCG CGG CAC GGC GCG GCG CGC TTC CGC         839
Arg Thr Thr Arg Ala Pro Pro Arg His Gly Ala Ala Arg Phe Arg
        210                 215                 220

SmaI
GTG CTG TAC CAC TCC CAC GTA TAC ACC CCG GGC GAT TCC TTT CTG         887
Val Leu Pro Tyr His Ser His Val Tyr Thr Pro Gly Asp Ser Phe Leu
    225                 230                 235                 240

CTA TCG GTG CGT CTG CAG TCT GAG TTT TTC GAC GAG GCT CCC TTC TCG    935
Leu Ser Val Arg Leu Gln Ser Glu Phe Phe Asp Glu Ala Pro Phe Ser
            245                 250                 255

GCC AGC ATC GAC TGG TAC TTC CTG CGG ACG GCC GGG GAC TGC GAC CTC GCG CTC  983
Ala Ser Ile Asp Trp Tyr Phe Leu Arg Thr Ala Gly Asp Cys Ala Leu
        260                 265                 270

ATC CGC ATA TAC GAG ACG TGC ATC TTC CAC CCC GAG GCA CCG GCC TGC    1031
Ile Arg Ile Tyr Glu Thr Cys Ile Phe His Pro Glu Ala Pro Cys
    275                 280                 285

CTG CAC CCC GCC GAC GCG CAG TGC AGC TTC GCG TCG CCG TAC CGC TCC    1079
Leu His Pro Ala Asp Ala Gln Cys Ser Phe Ala Ser Pro Tyr Arg Ser
            290                 295                 300
```

FIG. 3A-4

```
GAG ACC GTG TAC AGC CGG CTG TAC GAG CAG TGC CGC CCG GAC CCT GCC       1127
Glu Thr Val Tyr Ser Arg Leu Tyr Glu Gln Cys Arg Pro Asp Pro Ala
305                 310                 315                 320

GGT CGC TGG CCG CAC GAG TGC GAG GGC GGC TAC GCG GCG CCC GTT           1175
Gly Arg Trp Pro His Glu Cys Glu Gly Gly Tyr Ala Ala Pro Val
        325                 330                 335

GCG CAC CTG CGT CCC GCC AAT AAC AGC GTA GAC CTG GTC TTT GAC GAC       1223
Ala His Leu Arg Pro Ala Asn Asn Ser Val Asp Leu Val Phe Asp Asp
340                 345                 350

GCG CCC GCT GCG GCC TCC GGG CTT TAC GTC TTT GTG CTG CAG TAC AAC       1271
Ala Pro Ala Ala Ser Gly Leu Tyr Val Phe Val Leu Gln Tyr Asn
355                 360                 365

HindIII
GGC CAC GTG GAA GCT TGG GAC TAC AGC CTA GTC GTT ACT TCG GAC CGT       1319
Gly His Val Glu Ala Trp Asp Tyr Ser Leu Val Val Thr Ser Asp Arg
370                 375                 380

TTG GTG CGC GCG GTC ACC GAC CAC ACG CGC CCC GAG GCC GCA GCC GCC       1367
Leu Val Arg Ala Val Thr Asp His Thr Arg Pro Glu Ala Ala Ala Ala
385                 390                 395                 400

GAC GCT CCC GAG CCA GGC CCA CCG CTC ACC AGC GAG CCG GCG GGC GCG       1415
Asp Ala Pro Glu Pro Gly Pro Pro Leu Thr Ser Glu Pro Ala Gly Ala
        405                 410                 415
```

FIG. 3A-5

```
CCC ACC GGG CCC GCG CCC TGG CTT GTG GTG CTG GGC GCG CTT GGA    1463
Pro Thr Gly Pro Ala Pro Trp Leu Val Val Leu Val Gly Ala Leu Gly
        420                 425                 430
                     ==========================  TRANSMEMBRANE HELIX =======

CTC GCG GGA CTG GTG GGC ATC GCA GCC CTC GCC GTT CGG GTG TGC GCG    1511
Leu Ala Gly Leu Val Gly Ile Ala Ala Leu Ala Val Arg Val Cys Ala
        435                 440                 445
===============================================

CGC CGC GCA AGC CAG AAG CGC ACC TAC GAC ATC CTC AAC CCC TTC GGG    1559
Arg Arg Ala Ser Gln Lys Arg Thr Tyr Asp Ile Leu Asn Pro Phe Gly
        450                 455                 460

CCC GTA TAC ACC AGC TTG CCG ACC AAC GAG CCG CTC GAC GTG GTG GTG    1607
Pro Val Tyr Thr Ser Leu Pro Thr Asn Glu Pro Leu Asp Val Val Val
        465                 470                 475                 480

CCA GTT AGC GAC GAC GAC GAA TTT TCC CTC GAC GAA GAC TCT TTT GCG GAT    1655
Pro Val Ser Asp Asp Asp Glu Phe Ser Leu Asp Glu Asp Ser Phe Ala Asp
        485                 490                 495

GAC AGC GAC GAT GAC GGG CCC GCT AGC AAC CCC CCT GCG GAT GCC    1703
Asp Ser Asp Asp Asp Gly Pro Ala Ser Asn Pro Pro Ala Asp Ala
        500                 505                 510
```

FIG. 3A-6

```
TAC GAC CTC GCC GGC GCC CCA GAG CCA ACT AGC GGG TTT GCG CGA GCC     1751
Tyr Asp Leu Ala Gly Ala Pro Glu Pro Thr Ser Gly Phe Ala Arg Ala
515                          520                          525

CCC GCC AAC GGC ACG CGC TCG AGT CGC TCT GGG TTC AAA GTT TGG TTT     1799
Pro Ala Asn Gly Thr Arg Ser Ser Arg Ser Gly Phe Lys Val Trp Phe
        530                          535                          540

AGG GAC CCG CTT GAA GAC GAT GCC GCG CCA GCG CGG ACC CCG GCC GCA     1847
Arg Asp Pro Leu Glu Asp Asp Ala Ala Pro Ala Arg Thr Pro Ala Ala
545                          550                          555                  560

EcoNI
CCA GAT TAC ACC GTG GTA GCA GCG CGA CTC AAG TCC ATC CTC CGC TAG     1895
Pro Asp Tyr Thr Val Val Ala Ala Arg Leu Lys Ser Ile Leu Arg  *
        565                          570                         575

GCGCCCCCCC CCCCCCGCGC GCTGTGCCGT CTGACGGAAA GCACCCGCGT GTAGGGCTGC   1955
ATATAAATGG AGCGCTCACA CAAAGCCTCG TGCGGCTGCT TCGAAGGCAT GGAGAGTCCA   2015
CGCAGCGTCG TC                                                      2027
```

FIG. 4B

```
symbol comparison table :    DAYHOFF.DAT; gap penalty : 8
          1        10        20        30        40        50        60
    PRV   HSQLFSPGDTFDLMPRVVSDMGDSRENTFTATLDWYYARAPPRCLLYYVYEPCIYHPRAP
          **::** **** *   ::    :     *  *   *:* *    * *    :*  *:*** **
    VZV   HSHVFSVGDTFSLAMHLQYKI.H..EAPFDLLLEWLYVPIDPTCQPMRLYSTCLYHPNAP
          ****:  ** * *  ::**       ****   ::* ::       *  :*:* **::** **
    BHV   HSHVYTPGDSFLLSVRLQSEFFD..EAPFSASIDWYFLRTAGDCALIRIYETCIFHPEAP
             :: **: *    * ::     *   :   :*  : *   :      ** :**** *::**: *
    HSV   EAILFSPGETFSTNVSIHAIAHD..DQTYSMDVVWLRFLVPTSCAEMRIYESCLYHPQLP
          1        10        20          30        40        50

70        80        90       100       110
    PRV   ECLRPVDPACSFTSPARAALVARRAYASCSPLLGDRWLTACPFDAFGEEVH.........
          :**   ::  * ****  *  **    *  *      *     *      *
    VZV   QCLSHMNSGCTFTSPHLAQRVASTVYQNC..EHADNYTAYCLGISHMEPSFGLILHDGGT
           **    :  *** **    : * *  :*: *   : *      * *     *   *   :
    BHV   ACLHPADAQCTFASPYRSETVYSRLYEQCRPDPAGRWPHECEGAAYAAPVAHLRPANNSV
           ** **** *  *    :   :  * *  *         *  *    *   **  *    **
    HSV   ECLSPADAPC..AASTWTSRLAVRSYAGCSRTNP...PPRCSAEAHMEPVPGLAWQAASV
          60          70        80        90          100       110

120       130       140
    PRV   ....TNATADESGLYVLVMTHNGHVATWDYTLVAT
              :     *****: :  ****    **:* *
    VZV   TLKFVDTPESLSGLYVFYVYFNGHVEAVAYTVVST
           * * * *    ****** : :******  * :* *
    BHV   DLVFDDAPAAASGLYVFVLQYNGHVEAWDYSLVVT
          :* * **     ****: *:  * *: **     : *
    HSV   NLEFRDASPQHSGLYLCVVYVNDHIHAWGHITIST
              120       130       140     148
```

FIG. 10

```
1272      GGCCACGTGGAAGCTTGGGACTACAGCCTAGTCGTTACTTCGGACCGTTTGGTGCGCGGTCACC
                   HindIII
GACCACACGCGCCCCGAGGCCAGCCGCCCCGAGCGCTCCCGAGCCCAGGCCCACCGCTCACCAGCGAGCCGGCGGGCGCG
CCCACCGGGCCCGCGCCCTGGCTTGTGTGCTGGTGCGGCTTGGACTCGCGGGACTGGTGGGCATCGCAGCCCTC
GCCGTTCGGGTGTGCGCGCGGCCAAGCCAGAAGCGCACCTACGACATCCTCAACCCCTTCGGGCCCGTATACACC
AGCTTGCCGACCAACGAGCCGCTCGACGTGGTGCCAGTTAGCGACGAGTTAGCGACGAGAATTTTCCCTGACGAAGACTCTTTT
                                    P3                                TaqI
GCGGATGACGACAGCGACGATGACGGAGCCCCGCTAGCAACCCCCTGCGGATGCCTACGACCTCGCGGCGCCCAGAG
CCAACTAGCGGGTTTGCGCGAGCCCCGCCAACGGCACGCGCTCGAGTCGCTCTGGGTTCAAAGTTTGGTTTAGGGAC
                                                  TaqI    P4
CCGCTTGAAGACGATGCCGCGGACCCCGGCCGCAGCCAGAT'TACACCGTGGTAGCAGCCGACTCAAGTCC
ATCCTCCGCTAGGCGCCCCCCCCCGCGCTGTGCCGTCTGACGGAAAGCACCCGCGTGTAGGGCTGCATATAA    2027
   EcoNI
ATGGAGCGCTCACACAAAGCCTCGTGCGGCTGCTTCGAAGGCATGGAGAGTCCACGCAGCGTCGTC
```

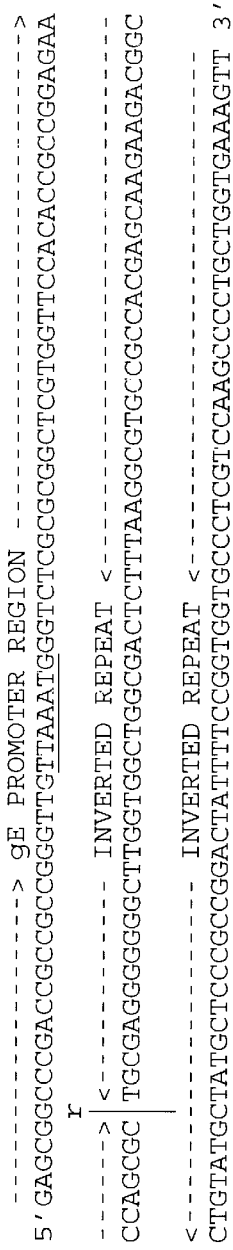

FIG. 13

```
          10         20         30         40         50         60
          |          |          |          |          |          |
CTACCACGCCGGGGCGACTGCTTCGTTATGCTGCAGAGACCGCGTTCGCCTTCCTGCCC
           Y  H  A  A  G  A  C  F  V  M  L  Q  T  T  A  F  A  S  C  P 70         80         90        100        110        120
          |          |          |          |          |          |
GCGCGTCGCGAACGACGCCTTTCGCTCCTGCCTGCACGCCGACACGCCCCGCTGCAG
  R  V  A  N  D  A  F  R  S  C  L  H  A  D  T  R  P  A  R  S 130        140        150        160        170        180
          |          |          |          |          |          |
CGAGCGGGCGCGAGCGCGGCCGCGGTCGAAAACCACGTGCTCTTCTCCATCGCCCATCCGCG
  E  R  R  A  S  A  A  V  E  N  H  V  L  F  S  I  A  H  P  R 190        200        210        220        230        240
          |          |          |          |          |          |
CCCAATAGACTCAGGGCTCTACTTTCTGCGTGCGGCATCTACGGCGGCACCGCGGGCAG
  P  I  D  S  G  L  Y  F  L  R  V  G  I  Y  G  G  T  A  G  S 250        260        270        280
          |          |          |          |
CGAGCGCCGCGAGACGTCTTTCCCTTGGCCGCGTTTGTACACA
  E  R  R  D  V  F  P  L  A  A  F  V  H
```

FIG. 14

```
symbol comparison table :    DAYHOFF.DAT; gap penalty : 8

1         10        20        30        40        50
BHV1  YHAAGD.CFVMLQTTAFASCPRVAN.AFRSCLHADTRP.ARSERRASAAVENHVLFSIA
       *:      ****  :  **** :: ****::    :   ******** :: ::
PRV   RLDPKRA.CYTREYAAEYDLCPRVHHEAFRGCLR...KR.EPLARRASAAVEARRLLFVS
        *     ***  :  ****     ** **  *       *       ** **
HSV1  YPMGHK.CPRVVHVVTVTACPRRPAVAFALCRATDSTH.SPAYPTLELNLAQQPLLRVQ
       *       ** *:    *** *   **  **               :*::
VZV   YADTVAFCFRSVQVIRYDGCPRIRTSAFISCRYKHSWHYGNSTDRISTEPDAGVMLKIT
              1         10        20        30        40        50

60        70        80        90 93
BHV1  HPRPIDSGLYFLRVGIYGG.TAGSERRRDVFPLAAFVH
       :* ** *:  *  *     *          *
PRV   RPAPPDAGSYVLRVR..NG.TTDLFVLTALVPPRGRPHÜ
       ******:    *       ::   *         *
HSV1  RATRDYAGVYVLRVWVGDAPNASLFVLGMAIAAEG
       :  : ****:* ***:: *  *:*:: ::   *
VZV   KPGINDAGVYVLLVRLDHSRSTDGFILGVNVYTAG
              70        80        90 94
```

BOVINE HERPESVIRUS TYPE 1 DELETION MUTANTS, VACCINES BASED THEREON, DIAGNOSTIC KITS FOR DETECTION OF BOVINE HERPESVIRUS TYPE 1

This application is a continuation of U.S. patent application Ser. No. 08/150,203 filed Dec. 6, 1993, now issued as U.S. Pat. No. 5,676,951 which was filed under 35 U.S.C. 371 as the national phase application of PCT/NL92/00097, filed Jun. 5, 1992, which claims the benefit of Netherlands Patent Application No. 9100989 filed on Jun. 7, 1991 in the name of Stitching Centraal Diergeneeskundig Instituut of Lelystad.

FIELD OF THE INVENTION

This invention relates to the fields of vaccination and diagnostics in connection with diseases which are caused by pathogens and involves the use of both the classic methods to arrive at a live attenuated vaccine or an inactivated vaccine and the modern methods based on DNA recombinant technology.

More specifically, the invention relates to live attenuated vaccines an inactivated vaccines for protecting animals, especially bovines, against bovine herpesvirus type 1 (BHV-1), these vaccines being so designed that they are not only safe and effective, but also create the possibility of distinguishing infected from non-infected animals in a vaccinated population.

Diagnostic kits which can be used for such a test for distinguishing infected from non-infected animals in a vaccinated population are also an aspect of the present invention.

BACKGROUND OF THE INVENTION

BHV-1, including the infectious bovine rhinotracheitis virus (IBRV) and the infectious pustular vulvovaginitis virus (IPVV), plays an important role in the development of respiratory diseases and fertility disorders in bovines. After an acute infection, BHV-1 often remains present in the host in a latent form. Latent virus can be reactivated under the influence of inter alia stress—which may or may not be accompanied by clinical phenomena—and subsequently excreted. As a consequence, infected cattle must be regarded as lifelong potential spreaders of BHV-1. BHV-1 occurs endemically in an estimated 75% of Dutch cattle farms. Especially older cattle are serologically positive.

There are a number of inactivated ("dead") vaccines and a number of attenuated ("live") vaccines available for inoculation against BHV-1 infections. Inactivated vaccines are prepared by killing the BHV-1 virus, for instance by heat treatment, irradiation or treatment with ethanol or formalin. However, these often give insufficient protection. Attenuated vaccines are prepared by a large number of passages on homologous (bovine) or on heterologous cells such as porcine or canine cells, and sometimes viruses are also treated physically or chemically then. In this way, unknown mutations/deletions develop in the virus genome, which often reduce the disease-producing properties of the virus. Attenuated live vaccines give better protection than inactivated vaccines, inter alia because they present more viral antigens to the immune system of the host. Another important advantage of live vaccines is that they can be administered intranasally, i.e., at the site where the first multiplication of the wild type virus occurs after infection. Yet, live vaccines leave room for improvement. Some live vaccines still seem to possess their abortogenic ability, which becomes manifest in particular after intramuscular administration. Moreover, probably all live vaccines remain latently present in the vaccinated cow. Also, there is a chance that if the vaccine differs only little from the wild-type virus, reversion to virulence will occur. But one of the major problems is that the BHV-1 vaccines cannot prevent infection by wild-type viruses. The result is that vaccinated cattle can also spread wild-type BHV-1.

For a proper BHV-1 control program, it is necessary to have disposal of an efficacious and safe vaccine that can be distinguished from wild-type virus, since the application of an efficacious vaccine can reduce the circulation of BHV-1 considerably and a test which can distinguish between a vaccine and a wild-type virus makes it possible to detect (and then remove) infected cattle in a vaccinated population.

Meanwhile, BHV-1 vaccines have been developed which seem to be safer than conventional vaccines and are distinguishable from wild-type virus. A thymidine kinase deletion mutant has been isolated which is abortogenic to a lesser degree, becomes latent less frequently and cannot be reactivated. Further, using recombinant DNA techniques, a BHV-1 vaccine has been constructed which has a deletion in the gene for glycoprotein gIII, which makes this vaccine distinguishable from wild-type BHV-1 by means of serological techniques. However, there are still some objections to these vaccines. On the one hand, the thymidine kinase gene is involved in the viral replication and less replication can lead to less protection. On the other hand, the glycoprotein gIII is important for generating protective antibodies, which makes a gIII deletion vaccine less effective. A practical problem is that intranasal administration, which generally gives the best protection, of recombinant vaccines is not allowed in some countries. Accordingly, there is a need for a vaccine which is safe as well as effective and yet can be distinguished from wild-type BHV-1, it being further desirable that at least one of such vaccines is based on a virus attenuated via a conventional route rather than a virus constructed by recombinant DNA techniques.

Now, via passages in cell cultures, a BHV-1 strain has been obtained which lacks the gene for glycoprotein gE. The first results of our research indicate that this gene is quite useful to make a serological distinction with regard to wild-type BHV-1 and that it is involved in the expression of virulence. Therefore, its deletion contributes to safety and may render the use of thymidine kinase deletions superfluous. The glycoprotein gE seems to be less important for induction of protection than the glycoprotein gIII. A conventionally attenuated BHV-1 strain which can be serologically distinguished from wild-type virus is unique. The location and DNA sequence of the gE gene described herein for the first time were not previously known, nor were oligonucleotides, polypeptides and oligopeptides that can be derived therefrom. A test for making a serological distinction on the basis of the gE gene is also unique.

An important advantage of this "conventional" gE deletion mutant ("conventional" refers to the use of a conventional method for isolating an attenuated virus) is that it will be possible to administer it intranasally in countries where this is forbidden as far as recombinant vaccines are concerned. Taking due account of the different views on safety, however, in addition to this conventional gE deletion vaccine, well-defined recombinant versions have been constructed as well. These recombinant vaccines also have a gE deletion—and may or may not have a deletion in the thymidine kinase gene as well—and can also be used as vectors for the expression of heterologous genes. All these recombinant vaccines can be distinguished from wild-type virus with the same gE-specific test. The use of a standard test for a set of different vaccines can be a great advantage in the combat of BHV-1 as an international effort. Such an approach has not been previously described in the field of BHV-1, vaccines.

Serological analysis of the anti BHV-1 response in cattle showed that an important fraction of the anti-gE antibodies are directed against a complex formed by glycoprotein gE and another BHV-1 glycoprotein: glycoprotein gI. Serological tests that can (also) demonstrate the presence of such complex-specific antibodies may therefore be more sensitive than tests that can only detect anti-gE antibodies. Cattle vaccinated with a single gE deletion mutant may produce anti-gI antibodies that can interfere with the detection of anti-gI/gE antibodies. Consequently, this invention also includes a vaccine with a gI/gE double deletion.

SUMMARY OF THE INVENTION

In the first place, this invention provides a deletion mutant of BHV-1 which has a deletion in the glycoprotein gE-gene. The words "a deletion in" intended to cover a deletion of the gene as a whole.

A preferred embodiment of the invention is constituted by a deletion mutant of BHV-1 which has a deletion in the glycoprotein gE-gene which has been caused by an attenuation procedure, such as the deletion mutant Difivac-1 to be described hereinafter.

Other preferred embodiments of the invention consist of a deletion mutant of BHV-1 comprising a deletion in the glycoprotein gE-gene which has been constructed by recombinant DNA techniques, such as the deletion mutants 1B7 or 1B8 to be described hereinafter.

Another preferred embodiment of the invention consists of a double deletion mutant of BHV-1 comprising a deletion of the glycoprotein gE-gene and a deletion in the glycoprotein gI-gene, such as the gI/gE double deletion mutant Difivac-IE to be described hereinafter.

Further, with a view to maximum safety, according to the invention a deletion mutant of BHV-1 is preferred which has a deletion in the glycoprotein gE-gene and a deletion in the thymidine kinase gene. The invention also covers a deletion mutant of BHV-1 which has a deletion in the glycoprotein gE-gene, the glycoprotein gI-gene and the thymidine kinase gene.

The invention provides a vaccine composition for vaccination of animals, in particular mammals, more particularly bovines, to protect them against BHV-1, comprising a deletion mutant of BHV-1 as defined hereinabove, and a suitable carrier or adjuvant. Said composition may be a live or an inactivated vaccine composition.

The invention is further embodied in a mutant of BHV-1 which has a deletion in the glycoprotein gE-gene and contains a heterologous gene introduced by recombinant DNA techniques.

Preferably, this concerns a mutant of BHV-1 which contains a heterologous gene introduced by recombinant DNA techniques at the location of the glycoprotein gE-gene, which heterologous gene is under the control of regulatory sequences of the gE-gene and is optionally attached to the part of the gE-gene which codes for a signal peptide. Said heterologous gene may also be under the control of a different promoter of BHV-1, or under the control of a heterologous promoter. When the mutant of BHV-1 has further deletions in addition to the deletion in the glycoprotein gE-gene, such as a deletion in the thymidine kinase gene and/or a deletion in the glycoprotein gI-gene, said heterologous gene may also be inserted at the location of this additional deletion(s). Plural insertions are another option, either together at the location of one deletion, or distributed over locations of several deletions.

The heterologous gene introduced preferably codes for an immunogenic protein or peptide of another pathogen, or for a cytokine which promotes the immune response. Examples of suitable cytokines are interleukin 2, interferon-alpha and interferon-gamma.

The invention also provides a (live or inactivated) vaccine composition for vaccination of animals, in particular mammals, more particularly bovines, to protect them against a (different) pathogen, comprising a mutant of BHV-1 having—therein a heterologous gene coding for an immunogenic protein or peptide of that other pathogen, and a suitable carrier of adjuvant. Of course, the protection may concern more than one pathogen, i.e. a multivalent vaccine wherein the mutant contains a plurality of heterologous genes.

The invention further relates to a composition comprising a recombinant nucleic acid comprising the glycoprotein gE-gene of BHV-1, a part of this glycoprotein gE-gene or a nucleotide sequence derived from this glycoprotein gE-gene. This composition can contain a cloning or expression vector having therein an insertion of a recombinant nucleic acid which comprises the glycoprotein gE-gene of BHV-1, a part of this glycoprotein gE-gene or a nucleotide sequence derived from this glycoprotein gE-gene.

The invention also comprises a composition comprising glycoprotein gE of BHV-1, a part of this glycoprotein gE, a peptide derived from this glycoprotein gE, or a complex of the glycoproteins gE and gI, and a composition comprising an antibody which is specific for glycoprotein gE of BHV-1, a part of this glycoprotein gE, a peptide derived from this glycoprotein gE, or a complex of the glycoproteins gE and gI. "Antibody" is understood to mean both a polyclonal antibody preparation and a monoclonal antibody preferred for most applications. The terms "a part of glycoprotein gE" and "a peptide derived from glycoprotein gE" are understood to mean gE-specific amino acid sequences which generally will have a length of at least about 8 amino acids.

The invention further relates to a diagnostic kit for detecting nucleic acid of BHV-1 in a sample, in particular a biological sample such as blood or blood serum, blood cells, milk, bodily fluids such as tears, lung lavage fluid, nasal fluid, sperm, in particular seminal fluid, saliva, sputum, or tissue, in particular nervous tissue, coming from an animal, particularly a mammal, more particularly a bovine, comprising a nucleic acid probe or primer having a nucleotide sequence derived from the glycoprotein gE-gene of BHV-1, and a detection means suitable for a nucleic acid detection assay.

Further, the invention relates to a diagnostic kit for detecting antibodies which are specific for BHV-1, in a sample, in particular a biological sample such as blood or blood serum, saliva, sputum, bodily fluid such as tears, lung lavage fluid, nasal fluid, milk, or tissue, coming from an animal, in particular a mammal, more in particular a bovine, comprising glycoprotein gE of BHV-1, a part of this glycoprotein gE, a peptide derived from this glycoprotein gE, or a complex of the glycoproteins gE and gI, and a detection means suitable for an antibody detection assay. Such a diagnostic kit may further comprise one or more antibodies which are specific for glycoprotein gE of BHV-1 or specific for a complex of the glycoproteins gE and gI of BHV-1.

The invention also relates to a diagnostic kit for detecting protein of BHV-1 in a sample, in particular a biological sample such as blood or blood serum, blood cells, mil, bodily fluids such as tears, lung lavage fluid, nasal fluid, sperm, in particular seminal fluid, saliva, sputum of tissue, in particular nervous tissue, coming from an animal, in particular a mammal, more in particular a bovine, comprising one or more antibodies which are specific for glycoprotein gE of BHV-1 or specific for a complex of the glycoproteins gE and gI of BHV-1, and a detection means suitable for a protein detection assay.

The invention further provides a method for determining BHV-1 infection of an animal, in particular a mammal, more in particular a bovine, comprising examining a sample coming from the animal, in particular a biological sample such as blood or blood serum, blood cells, sperm, in particular seminal fluid, saliva, sputum, bodily fluid such as tears, lung lavage fluid, nasal fluid, milk, or tissue, in particular nervous tissue, for the presence of nucleic acid comprising the glycoprotein gE-gene of BHV-1, or the presence of the glycoprotein gE of BHV-1 or a complex of the glycoproteins gE and gI of BHV-1, or the presence of antibodies which are specific for the glycoprotein gE of BHV-1 or specific for a complex of the glycoproteins gE and gI of BHV-1. The sample to be examined can come from an animal which has not been previously vaccinated with a vaccine composition according to the invention or from an animal which has previously been vaccinated with a vaccine preparation according to the invention.

DETAILED DESCRIPTION OF THE INVENTION

The invention relates to a set of BHV-1 vaccines, both live and inactivated, which have in common that they lack the glycoprotein gE gene in whole or in part. This set comprises both a natural gE deletion mutant and constructed gE deletion mutants which may or may not also comprise a deletion of the thymidine kinase gene and/or the glycoprotein gI gene, and constructed gE deletion mutants which are used as vectors for heterologous genes. The invention further relates to nucleotide sequences encoding the BHV-1 glycoprotein gE-gene, oligonucleotides derived from these sequences, the glycoprotein gE itself, peptides which are derived therefrom and (monoclonal or polyclonal) antibodies which are directed against the gE glycoprotein and peptides derived therefrom. The invention also relates to complexes of the glycoproteins gE and gI of BHV-1, and to antibodies directed against such complexes.

These materials according to the invention can be used for:
1) the vaccination of cattle against diseases caused by BHV-1, such that a distinction can be made between BHV-1 infected animals and vaccinated animals; the conventional and the constructed vaccine can be used side by side;
2) the vaccination of cattle against both BHV-1 diseases and diseases caused by other pathogens of which coding sequences for protective antigens can be incorporated into the BHV-1 deletion mutants;
3) testing blood, serum, milk or other bodily fluids from cattle to determine serologically or by means of nucleic acid detection techniques (e.g. PCR) whether they have been infected by a wild-type BHV-1 or have been vaccinated with a gE deletion mutant.

Synthesis of oligopeptides, polypeptides and glycoproteins derived from the coding sequence of the glycoprotein gE-gene and the glycoprotein gI-gene of BHV-1

The results of the DNA sequence analysis, described in the examples, of the glycoprotein gE-gene (FIG. 3A) and the isolated DNA fragments which code for this gene, make it possible, using standard molecular-biological procedures, both to synthesize peptides of the gE protein (oligo or polypeptides) and to express the gE protein in its entirety or in large parts via the prokaryotic route (in bacteria) or via the eukaryotic route (for instance in murine cells). Via these routes, gE-specific antigen can be obtained which can for instance serve for generating gE-specific monoclonal antibodies (Mabs). Furthermore, gE-specific antigen (and gE-specific Mabs) can be used in serological tests to enable a distinction to be made between animals vaccinated with a BHV-1 gE deletion vaccine and animals infected with wild-type BHV-1 virus.

The results of the partial DNA sequence analysis of the glycoprotein gI gene—described in the examples—and the isolated DNA fragments that code for this gene, together with the eukaryotic cells expressing glycoprotein gE, allow the expression of the gI/gE complex in eukaryotic cells (See FIGS. 13 and 14). This glycoprotein complex can be used to produce gI/gE specific monclonal antibodies. The gI/gE complex can also be used as antigen in serological tests to differentiate between cattle vaccinated with a single gE BHV-1 deletion mutant or with a double gI/gE BHV-1 deletion mutant and cattle infected with wild type BHV-1 virus.

gE specific peptides

On the basis of a known protein coding sequence, by means of an automatic synthesizer, polypeptides of no less than about 40–50 amino acids can be made. Now that the protein coding sequence of the gE glycoprotein of BHV-1 strain Lam has been unraveled (FIG. 3A), polypeptides of this BHV-1 gE glycoprotein can be synthesized. With such polypeptides, according to standard methods, experimental animals such as mice or rabbits can be immunized to generate gE-specific antibodies. Further, using these gE-specific peptides, the locations where anti-gE antibodies react with the gE protein (the epitopes) can be further specified, for instance with the PEPSCAN method (Geysen et al., 1984 Proc. Natl. Acad. Sci. USA 81, 3998–4002). gE specific oligopeptides can also be used in serological tests which demonstrate anti-gE antibodies.

Prokaryotic expression of gE

For the synthesis of the gE protein in bacteria (i.e. the prokaryotic expression of gE), DNA fragments which code for the glycoprotein gE or for parts thereof must be cloned into prokaryotic expression vectors. Prokaryotic expression vectors are circular DNA molecules which can maintain themselves in a bacterium as a separately replicating molecule (plasmid). These expression vectors contain one or more marker genes which code for an antibiotic resistance and thus enable the selection for bacteria with the expression vector. Further, expression vectors comprise a (often controllable) promoter region behind which DNA fragments can be ligated which are then expressed under the influence of the promoter. In many current prokaryotic expression vectors, the desired protein is expressed while fused to a so-called carrier protein. To that end, in the vector there is located behind the promoter the coding sequence for the carrier protein, directly adjacent to which the desired DNA fragment can be ligated. Fusion proteins are often more stable and easier to recognize and/or to isolate. The steady-state level which a particular fusion protein can attain in a certain bacterial strain differs from fusion to fusion and from strain to strain. It is customary to try different combinations.

Eukaryotic expression of the glycoprotein gE-gene

Although prokaryotic expression of proteins offers some advantages, the proteins lack the modifications, such as glycosylation and the like, which occur in eukaryotic cells. As a result, eukaryotically expressed protein is often a more suitable antigen. For the heterologous expression of proteins in eukaryotic cells, such as murine cells, use is made of eukaryotic expression vectors. These vectors are plasmids which can not only be multiplied in *E. coli* cells but also subsist stably in eukaryotic cells. In addition to a prokaryotic selection marker, they also comprise a eukaryotic selection marker. Analogously to the prokaryotic expression vectors, eukaryotic expression vectors contain a promoter region behind which desired genes can be ligated. However, the promoter sequences in eukaryotic vectors are specific for eukaryotic cells. Moreover, in eukaryotic vectors fusion to carrier proteins is utilized only rarely. These vectors are introduced into the eukaryotic cells by means of a standard transfection method (F. L. Graham and A. J. van der Eb, 1973, Virology 52, 456–467). In addition to the eukaryotic plasmid vectors, there are also viral vectors, where the heterologous gene is introduced into the genome of a virus (e.g. retroviruses, herpesviruses and vaccinia virus). Eukaryotic cells can then be infected with recombinant viruses.

In general, it cannot be predicted what vector and cell type are most suitable for a particular gene product. Mostly, several combinations are tried.

Eukaryotic expression of both the glycoprotein gE and the glycoprotein gI

The final structure that a protein obtains, is depending on its primary amino acid sequence, its folding, its posttranslational modifications etc. An important factor that contributes to structure of a protein is its interaction with one or more other proteins. We have found that also BHV-1 glycoprotein gE forms a complex with at least one other glycoprotein: BHV-1 glycoprotein gI. The first indication for such a complex came from our results with candidate anti-gE Mabs 1, 51, 67 75 and 78 (See table 2). These Mabs did not react with Difivac-1, nor with Lam gE⁻ but also failed to recognize glycoprotein gE-expressing 3T3 cells. However, these Mabs did react with gE-epressing 3T3 cells after infection with Difivac-1, showing that complementing factors are needed to give glycoprotein gE the proper antigenic conformation for these Mabs. In some of our radio-immunoprecipitation experiments with Mab 81 we found coprecipitation of a protein with an apparent molecular weight of 63 kD. In view of the fact that the herpes simplex virus glycoprotein gE forms a complex with a protein with a comparable molecular weight (HSV1 glycoprotein gI), we inferred that BHV-1 glycoprotein gE forms a complex with the BHV-1 homolog of glycoprotein gI. To study this BHV-1 gE/gI complex and to produce gE antigen with the proper antigenic structure we expressed both glycoproteins in one eukaryotic cell. For this we applied the same procedure as described for the eukaryotic expression of glycoprotein gE alone. The only additional prerequisite is the use of expression vectors with different eukaryotic selectable markers.

Serological tests

Serological methods for making a distinction between cattle vaccination with Difivac-1 and cattle infected with wild-type BHV-1 on the basis of antibodies against gE are preferably based on the use of monclonal antibodies directed against gE. These can be used in the following manners:

a) According to the principle described by Van Oirschot et al. (Journal of Virological Methods 22, 191–206, 1988). In this ELISA for the detection of gI antibodies against the virus of Aujeszky's disease, antibodies are demonstrated by their blocking effect on the reaction of two Mabs having two different epitopes on gI. The test is carried out as follows. Microtiter plates are coated with Mab 1, overnight at 37° C., after which they are stored, e.g. at 4° C. or −20° C. The serum to be examined is preincubated with antigen in separate uncoated microtiter plates, e.g. for 2 h at 37° C. The Mab 1-coated plates are washed, e.g. 5 times, after which Mab 2 coupled to horseradish peroxidase (HRPO) is added to these plates. Then the preincubated serum-antigen mixtures are transferred to the plates in which the two Mabs are located, followed by incubation, e.g. for 1 h at 37° C. The plates are washed and substrate is added to each well. After e.g. 2 h at room temperature, the plates are spectrophotometrically read. Four negative control sera and four serial dilutions of a positive serum are included on each plate. The serum which has an optical density (OD) value of less than 50% of the average OD value of the 4 negative control sera which have been examined on the same plate, is considered positive.

b) According to the Indirect Double Antibody Sandwich (IDAS) principle. Here, microtiter plates are coated with an Mab or a polyclonal serum directed against the gE protein. Incubation with a gE antigen preparation results in gE binding to the coating. Antibodies specifically directed against gE in the bovine serum to be examined subsequently bind to the gE. These bound antibodies are recognized by an anti-bovine immunoglobulin conjugate. The antibodies in this conjugate are covalently bound to peroxidase enzyme. Finally, the bound conjugate is visualized by addition of a chromogenic substrate. The specificity of the reaction is checked by carrying out the same procedure with a gE-negative control preparation instead of a gE-antigen preparation. On each microtiter plate, positive and negative control sera are included. The test is valid if the positive serum scores positive in a certain dilution. A serum is positive if it scores an OD which is 0.2 higher than the standard negative control serum.

c) According to the IDAS principle as described under 2, but after incubation of the serum to be examined an anti-gE Mab/HRPO is used instead of the anti-bovine immunoglobulin conjugate. An anti-gE peptide serum or an anti-gE polyclonal serum may be used instead of the anti-gE Mab. The plates are washed and to each well a chromogenic substrate is added. After e.g. 2 h at room temperature, the plates are spectrophotometrically read. Four negative control sera and four serial dilutions of a positive serum are included on each plate. The serum which has an OD value of less than 50% of the average OD value of the 4 negative control sera which have been examined on the same plate, is considered positive.

d) According to the principle of a blocking ELISA, whereby virus antigen which may or may not be purified is coated to the microtiter plate overnight. In these plates, the serum to be examined is incubated for, e.g. one hour or longer at 37° C. After a washing procedure, an anti-gE Mab is added to the plates, followed by incubation for e.g. 1 h at 37° C. An anti-gE peptide serum or an anti-gE polyclonal serum may be used instead of the anti-gE Mab. The plates are washed and to each well a chromogenic substrate is added. After e.g. 2 h at room temperature, the plates are read spectrophotometrically. Four negative control sera and four serial dilutions of a positive serum are included on each plate. The serum which has an OD value of less than 50% of the average OD value of the 4 negative control sera which have been examined on the same plate, is considered positive.

In all the above arrangements, conventionally grown virus antigen which contains gE can be used, but so can gE-antigen which is expressed via prokaryotes or eukaryotes. Alternatively, oligopeptides based on the BHV-1 gE sequence could be used in the above diagnostic tests instead of conventional antigen. In addition, such oligopeptides could be used for the development of a so-called "cow-side" test according to the principle described in an article by Kemp et al., Science 241, 1352–1354, 1988. Such a test would then be based on a binding of the antigenic sequence of the oligopeptide by antibodies directed against gE, present in infected animals. For such a test, the oligopeptide would have to be coupled to an Mab directed against bovine erythrocytes.

Nucleic acid analysis using the polymerase chain reaction

Oligonucleotides (probes and primers) can for instance be used in the polymerase chain reaction to make a distinction between vaccinated and infected animals. The polymerase chain reaction (PCR) is a technique whereby nucleic acids of a pathogen can be multiplied billions of times in a short time (De polymerase kettingreactie, P. F. Hilderink, J. A. Wagenaar, J. W. B. van der Giessen and B. A. M. van der Zeijst, 1990, Tijdschrift voor Diergeneeskunde deel 115, 1111–1117). The gE oligonucleotides can be chosen such that in a gE positive genome a different product is formed than in a gE negative genome. The advantage of this is that also an animal which has been vaccinated with a gE deletion vaccine gives a positive signal in a PCR test. However, this approach depends on the presence of nucleic acids of the virus in a sample, for instance blood, coming from the animal to be tested.

After an acute BHV-1 infection, there is a great chance that BHV-1 specific nucelic acids can be demonstrated in the blood, but it has not been determined yet whether BHV-1 nucleic acids can also be demonstrated in the blood during latency.

The use of BHV-1 as a vector

For expressing heterologous genes in the BHV-1 genome, it is necessary to have disposal of exact information on the area where the heterologous gene is to be inserted. There should not be any disturbance of essential sequences, and regulatory sequences must be available for the expression of the heterologous gene. In principle, the glycoprotein gE-gene is a suitable place to express heterologous genes. The gE-gene is not essential, hence there is no objection to replacing the gE gene by the heterologous gene. As a consequence, the heterologous gene can be so positioned that it will be under the influence of the regulatory sequences of the gE gene. However, it is not necessary to use the regulatory sequences of the gE-gene. The expression of heterologous genes may be controlled alternatively by other, e.g. stronger regulatory sequences of different genes. It is also possible to ligate the heterologous gene to the (export) signal peptide of the gE gene, so that the secretion of the heterologous gene product can be influenced. It is clear that detailed knowledge of the gE gene and the gE protein affords the possibility of using BHV-1 as a vector in a very measured manner. The vectors developed can moreover be serologically distinguished from wild-type. The construction of BHV-1 mutants which express heterologous genes can be carried out in the same manner as the construction of gE deletion mutants shown in the examples. However, the deletion fragments should then be replaced with a fragment on which a heterologous gene is located at the location of the deletion.

EXAMPLES

1) Isolation and identification of a natural gE deletion mutant a) Isolation of a natural mutant Genomic DNA was isolated from a number of conventionally attenuated vaccines according to standard methods and analyzed using restriction enzymes. In particular, we searched for genome deviations which would be suitable to enable distinction from wild-type BHV-1 virus.

Attention was directed in particular to the $U_S$ region of the BHV-1 genome, because in that region—by analogy with the herpes simplex virus—probably a number of genes coding for non-essential glycoproteins are located [Identification of a herpes simplex virus 1 glycoprotein gene within a gene cluster dispensable for growth in cell culture, R. Longnecker, S. Chatterjee, R. J. Whitley and B. Roizman (1987) Proc. Natl. Acad. Sci. 84, 4303–4307].

A batch of a BHV-1 vaccine coming from the University of Zagreb, Yugoslavia (Lugovic et al., Veterinarski Arhiv 55, 241–245, 1985), after a great number of passage on bovine embryonal kidney cells and embryonal bovine trachea cells (Ebtr), proved to have a deviant $U_S$ region in addition to a normal $U_S$ region. This vaccine moreover appeared to form both large and small plaques on Ebtr cells. From this mixed population, a virus with a deviant $U_S$ region was isolated by three limiting dilution steps, with small plaques being chosen each time. The virus isolated via this route was examined further and called Difivac-1. It was deposited with Institut Pasteur, Paris, France, on May 27, 1992, deposit number I-1213.

b) Identification of the deletion in the gE gene in Difivac-1

For further analysis of this deviation in the $U_S$ region, genomic DNA of Difivac-1 was isolated according to standard methods and subjected to Southern blot analysis (FIG. 1A). Hybridization of this blot with a $^{32}P$ labeled wild-type HindIII K fragment confirmed that this fragment, located centrally in the $U_S$ region, is some 1.0 kilobase (kb) shorter in Difivac-1. Moreover, by this analysis, the position of the missing part could be approximately (FIG. 1B). For further analysis of this deletion, the $U_S$ region of the wild-type BHV-1 strain Lam was isolated and cloned into prokaryotic vectors. To that end, according to standard methods, genomic DNA of the Lam strain (FIG. 2A) was isolated and cloned into the vectors pUC18, pACYC and pBR322 (FIG. 2B). A physical map of the area around the supposed position of the deletion was composed (FIG. 2C). Starting from this physical map, subclones suitable for the determination of the nucleotide sequence of this area were constructed in the vectors pKUN19 and pUC18 (FIG. 2D). Using these subclones, the nucleotide sequence of the two strands of the entire area (indicted in FIG. 2C) was determined using the Sanger method. This nucleotide sequence (SEQ ID NO:1) was analyzed using the PC/Gene program. From the conceptual translation, it appeared that nucleotides (nt) 168 through nt 1893 code for an open reading frame of 575 amino acids (FIG. 3A). Further analysis showed that this amino acid sequence has the characteristics of a transmembrane glycoprotein as is shown in FIG. 3B. The fact is that the first 26 amino acids (aa) are recognized as a typically eukaryotic export signal and the area between aa 423 and aa 450 is recognized as a transmembrane region. In addition, three potential N-bound glycosylation sites occur in this sequence. This predicted amino acid sequence exhibits clear similarities to the glycoprotein gE-gene of herpes simplex virus (HSV); see FIGS. 4A and 4B. These and other similarities justify the conclusion that the gene found is the gE homologue of BHV-1. For this reason, the gene is called gE.

To determine to what extent this BHV-1 gE-gene is missing in Difivac-1, the p318 fragment was isolated. The p318 fragment starts on the AluI site 55 nt before the postulated BHV-1 gE open reading frame and ends 133 nt behind it. Genomic Difivac-1 DNA was analyzed with this p318 fragment using Southern blot hybridization. This revealed that Difivac-1 contains no p318 detectable sequences (FIG. 5). This experiment confirmed that Difivac-1 contains a deletion and clearly demonstrates that this deletion extends throughout the entire gE gene.

To determine the size and the position of the deleted region, genomic sequences covering the $U_S$ region of Difivac-1 were cloned into prokaryotic vectors. See FIG. 11C. The 14.5 kb EcoRI fragment was cloned into the pACYC vector and named p775. The 7.4 kb HindIII fragment was independently cloned into the pUC18 vector and named p728. From clone p728 two subclones were isolated: the 1.4 kb PstI fragment in clone p737 and the 350 bp AluI-PstI fragment in clone p754. Restriction enzyme analysis and Southern blot analysis of these clones (data not shown), demonstrated that the gE deletion in Difivac-1 is 2.7 kb long, starting just 5' from the gE gene and ending at the border of the $U_S$ region. These 2.7 kb have been replaced by a duplication of a 1 kb segment, located in the $U_S$ region opposite to the gE gene, as an aberrant extension of the repeat region. See FIG. 11B. To confirm the results of this analysis and to determine the exact recombination point, the nucleotide sequence of most of the insert of clone p754 was determined and compared with the wild type sequences. See FIG. 12. This analysis showed that the recombination point is located 77 bp upstream from the start codon of the gE gene.

c) Evaluation of safety and efficacy of Difivac-1

Difivac-1 was tested in BHV-1 seronegative specific pathogen free calves of seven week old. Eight calves were intranasally vaccinated with $10^5$ $TCIF_{50}$ in 2 ml, of which 1 ml was sprayed in each nostril. Eight BHV-1 seronegative specific pathogen free calves of seven week old, that were housed in a separate isolation unit, were given 2 ml of culture medium intranasally, and served as unvaccinated controls. Five weeks after vaccination, vaccinated and control calves were challenged intranasally with $10^7$ $TCID_{50}$ of the highly virulent BHV-1 strain Iowa. Six weeks after challenge all the calves were treated intramuscularly with dexamethasone for 5 days to reactivate putative latent virus. Clinical signs, rectal temperatures and body growth were monitored. Virus isolations were performed from nasal swabs, and neutralizing antibody titres were determined in serum.

After vaccination, behaviour, appetite, rectal temperatures and growth rates of the calves remained normal, but the vaccinated calves had some serious nasal discharge and some hypersalivation. Lesions in nasal mucosa were not observed. Difivac-1 was excreted from nasal swabs after vaccination (FIG. 17). All vaccinated calves produced neutralizing antibodies to BHV-1.

After challenge, all unvaccinated control calves showed apathy, loss of appetite, ocular and nasal discharge, reddening of the gingiva of the lower jaw, severe lesions of the nasal mucosae until 14 days after challenge, and a growth arrest of 4 days. The vaccinated calves had small, quickly healing lesions of the nasal mucosae and had no growth arrest. The daily clinical scores, the rectal temperature and growth development after challenge are given in FIGS. 18, 19 and 20. After challenge, all calves shed virus from their nose, but the amount and period of virus excretion was markedly reduced in vaccinated calves (FIG. 21). A secondary antibody response developed in vaccinated calves and the unvaccinated calves all produced antibodies after challenge.

After reactivation, the challenge virus was isolated from one vaccinated calf and from 5 unvaccinated claves. Difivac-1 could not be reactivated.

The above results demonstrate that Difivac-1 hardly induced any sign of disease in young calves and was not reactivatable. Difivac-1 markedly reduced the severity of disease and the amount of virus excretion after challenge.

In conclusion, Difivac-1 is a safe and efficacious vaccine for use in cattle against BHV-1 infections.

2) Construction of recombinant gE deletion mutants of BHV-1

In order to be able to have disposal of differentiatable BHV-1 vaccines which are molecularly better defined than Difivac-1 and which, if so desired, contain a deletion in for instance the thymidine kinase gene, in addition to a deletion in the gE gene, recombinant gE deletion mutants were constructed, in addition to Difivac-1. Starting from the determined position of the glycoprotein gE-gene and using the cloned DNA fragments which flank the gE-gene, a gE deletion fragment could be constructed. Using a standard technique (F. L. Graham and A. J. van der Eb, 1973, Virology 52, 456–467), this deletion fragment could be recombined in the genome of a wild-type BHV-1 strain, resulting in a gE deletion mutant.

a) The construction of the gE deletion fragment

For the construction of the gE deletion fragment, a fragment was aimed for which, on the one hand, lacks the entire gE sequence and, on the other, contains sufficient flanking sequence to allow recombination with the wild-type genome. At the 5' (upstream) side, the 1.2 kb PstI-AsuII fragment which ends 18 nt before the start codon of the gE gene was chosen. For the 3' (downstream) fragment the 1.2 kb EcoNI-DraI fragment was chosen, which starts 2 nt before the stop condon of the gE gene (FIG. 6).

For the construction of the gE deletion fragment, the 1.4 kb PstI-SmaI fragment coming from the 8.4 kb HindIII K fragment of BHV-1 strain Lam, located at the 5' side of the gE gene, was subcloned into the SmaI and PstI site of plasmid pUC18. This clone was called p515. The EcoNI-SmaI fragment located on the 3' side of gE and coming from the 4.1 kb HindIII-EcoRI clone was cloned into the unique AsuII site of p515. Thus, the construction of the gE deletion fragment was completed and the clone so constructed was called p519. Although in principle the entire PstI-SmaI insert of p519 could be used as gE deletion fragment, this is not advisable. The fact is that the PstI-SmaI extends approx. 100–150 base pairs (bp) into the repeat sequence which flanks the $U_S$ region. This piece of 100–150 bp could recombine with the repeated sequence on the other side of the $U_S$ area where the gE gene is not located and could thus yield undesirable recombination products. For that reason, the PstI-DraI fragment was chosen for the recombination experiment, so that 100 bp of the repeat are removed.

b) Recombination of the gE deletion fragment with the genome of wild-type BHV-1

In order to effect the recombination between the constructed gE deletion fragment and the genome of wild-type BHV-1, microgram amounts of the two DNA molecules are cotransferred to Embryonal bovine trachea (Ebtr) cells according to the standard method of F. L. Graham and A. J. van der Eb (1973, Virology 52, 456–67). Cellular recombination mechanisms lead to the recombination of a small percentage of the DNA molecules (2–4%) which have been incorporated by the cells. For the selection of the recombined gE deletion mutants, the virus mixture that is formed after transfection is disseminated on a fresh Ebtr cell culture. In most cases, the separate virus populations which thereby develop (plaques) originate from one virus. For the isolation of gE deletion mutants of BHV-1 strain Lam, 230 of these plaques were isolated and examined according to standard immunological methods with BHV-1 specific monoclonal antibodies (Mabs) which do not react with Difivac-1 infected cells. These Mabs are directed against the glycoprotein gE. Five of the 230 plaques did not react with these Mabs. The DNA of these 5 plaques was further investigated.

c) DNA analysis of the constructed gE deletion mutants of BHV-1 strain Lam

DNA preparations of 3 (1B7, 1B8 and 2H10) of the above mentioned 5 candidate gE deletion mutants were further examined using the standard Southern blot analysis technique (Sambrook et al. 1989). Double digestions of these DNA preparations with PstI and DraI, followed by gel electrophoresis and Southern blot hybridization with the 2.3 kb PstI-DraI deletion fragment as probe show that the gE gene of the genome of virus populations 1B7 and 1B8 has been removed exactly in the desired manner; see FIGS. 7A and 7B. Population 2H10 has a deviant PstI-DraI fragment. Southern blot hybridizations with a gE-specific probe show that no gE sequences are located in any of the three DNA preparations (results are not shown). BHV-1 virus populations 1B7 and 1B8 are intended recombinant gE deletion mutants. BHV-1 virus population 1B7 has been tested for vaccine properties.

Bovine Herpes Virus Type I (BHV-1) mutant 1B7 was deposited on Sep. 15, 1999 with the Collection Nationale de Cultures de Microorganismes (CNCM) at the Institut Pasteur, 28 Rue due Docteur Roux, 75724 Paris Cedex 15, France, under Registration No. I-2313.

d) Construction of thymidine kinase/gE double deletion mutants

Because BHV-1 recombinant deletion mutants with a deletion in only one gene may not be of sufficiently reduced virulence, deletions were also provided in the thymidine kinase (TK) gene of the BHV-1 strains Lam and Harberink. These mutants were constructed in an analogous manner to that used for the above-mentioned gE deletion mutants (results are not shown). These TK deletion mutants have been used to construct TK/gE double deletion mutants.

e) Construction of glycoprotein gI/glycoprotein gE double deletion mutants

Because cattle vaccinated with a single gE deletion mutant may produce anti-gI antibodies that can interfere with the detection of anti gI/gE antibodies (discussed below), we also invented a vaccine with a gI/gE double deletion. Such a gI/gE double deletion mutant can be constructed using the same procedures used for the construction of the gE single deletion mutant. Partial nucleotide sequence analysis of the upstream end of the 1.8 kb PstI fragment—that covers the 5' end of the gE gene—reveated an open reading frame with significant homology to gI homologs found in other herpesviruses. See FIGS. 13 and 14. Using the 350 bp SmaI-PstI fragment that encompasses the putative 5' end of the gI gene and the EcoNI-SmaI fragment, located downstream of the gE gene, a gI/gE deletion fragment can be constructed. This fragment can be recombined with the wild type genome to yield a BHV-1 gI/gE deletion mutant. See FIG. 16. The 80–90 amino acids that—theoretically—may still be produced, will not be able to elicit antibodies that can interfere with the detection of anti-gI/gE antibodies. Further sequence analysis of the gI gene will allow the construction of a gI deletion that covers the complete gI coding region. This gI/gE double deletion mutant has been named Difivac-IE.

f) Evaluation of safety and efficacy of the Lam gE$^-$ and the Lam gE$^-$, TK$^-$ mutants Vaccine properties of the Lam gE$^-$, and the Lam gE$^-$, TK$^-$ BHV-1 mutant strains were tested in seven-week-old, BHV-1 seronegative, specific pathogen free calves. Each mutant strain was sprayed intranasally in 6 calves. Each calf was given a total dose of $10^5$ TCID$_{50}$ in 2 ml culture medium, of which 1 ml was sprayed in each nostril. Another 6 calves were sprayed intranasally with virus-free culture medium, and served as unvaccinated controls. Five weeks after vaccination all calves, vaccinated and controls, were challenged intranasally with $10^7$ TCID$_{50}$ of the highly virulent BHV-1 strain Iowa. After vaccination and after challenge, clinical signs, rectal temperatures and body weight were monitored. Nasal swabs were taken to determine the number of days of nasal virus shedding.

After vaccination, behaviour, appetite, rectal temperature and growth rates of the calves remained normal. Serous nasal discharge and small lesions of the nasal mucosa were observed in all vaccinated calves. Virus could be isolated from the noses of the vaccinated calves for approximately 7 days (Table 1).

After challenge, all unvaccinated control calves showed apathy, loss of appetite, ocular and nasal discharge, reddening of the gingiva of the lower jaw, severe lesions of the nasal mucosae and growth was reduced. Calves vaccinated with Lam gE$^-$, TK$^-$ all developed some nasal discharge and showed some minor lesions of the nasal mucosae. Not all calves vaccinated with Lam gE$^-$ did develop nasal discharge or lesions of the nasal mucosae. Apathy, loss of appetite, or other clinical symptoms of disease were not observed with vaccinated calves. Rectal temperature, growth and clinical score after challenge are shown in FIGS. 22, 23 and 24. Unvaccinated calves shed virus from the nose 2 times longer than vaccinated calves (Table 1).

The above results demonstrate that the Lam gE$^-$ and the Lam gE$^-$, TK$^-$ BHV-1 mutant strains hardly induced any clinical sign of disease in young calves. Both mutant strains prevented sickness after challenge and reduced the period of nasal virus shedding with 50%.

Lam gE$^-$ and Lam gE$^-$, TK$^-$ BHV-1 mutant strains are safe and efficacious for use as a vaccine in cattle against BHV-1 infections.

3) Prokaryotic expression of gE

For the prokaryotic expression of the BHV-1 glycoprotein gE-gene, so far use has been made of pGEX expression vectors (D. B. Smith and K. S. Johnson, Gene 67 (1988) 31–40). pGEX vectors code for the carrier protein glutathione S-transferase (GST) from Schistosoma japonicum which is under the influence of the tac promoter which can be induced to expression by Isopropylthiogalactoside (IPTG). An example of a GST-gE fusion protein is the product of construct pGEX-2T600s3 (FIG. 8A). In this construct, using standard molecular-biological techniques (Sambrook et al. 1989), a 600 bp SmaI fragment which codes for an N-terminal region of 200 amino acids of the gE protein was ligated behind the GST gene. This construct was designed in triplicate, with each time a different reading frame of the 600bp fragment being ligated to the GST. All three constructs were introduced into Escherichia coli strain DH5α, induced with IPTG and the proteins formed were transferred to nitrocellulose after polyacrylamide gel electrophoresis by means of Western blotting. Immunological detection with anti-GST antibodies demonstrated that only the proper reading frame (No. 3) which codes for the gE protein area leads to the expression of a prominent fusion protein of the predicted size of 27 k (GST)+20 k (gE)=47 k. Three of the Mabs isolated by us that do not react with Difivac-1 recognize the 47 kD GST-gE fusion protein in a Western blot; see FIG. 8B 4) Eukaryotic expression of the glycoprotein gE-gene For the eukaryotic expression of the glycoprotein gE-gene, heretofore inter alia the vector pEVHis has been chosen. The pEVHis vector has, as eukaryotic marker, the HisD gene coding for the histidinol dehydrogenase [EC 1.1.1.23] (C. Hartmann and R. Mulligan, 1988, Proc. Natl. Acad. Sci. USA 85, 8047–8051) which causes cells to survive the toxic concentration of 2.5 mM histidinol. The vector moreover comprises the promoter region of the immediate early gene of the human cytomegalovirus (HCMV), with unique restriction enzyme sites located behind it. For the construction of a pEVHis/gE expression vector, use was made of a fragment comprising the entire coding region of the glycoprotein gE-gene. It starts on the AluI site 55 bp before the postulated open reading frame of gE and ends 133 bp behind it. This region was cloned behind the HCMV promoter of the pEVHis vector, whereby the construct pEVHis/gE was formed (FIG. 9). The pEVHis/gE was amplified in *E. coli* DH5α cells and purified by means of a cesium chloride gradient (Sambrook et al., 1989). This purified DNA was transfected to Balb/C-3T3 cells according to the method of Graham and Van der Eb. Transformed cells were selected with histidinol, whereafter twenty histidinol resistant colonies could be isolated. These colonies were examined with Mab 81 by means of an Immuno Peroxidase Monolayer Assay (IPMA). Four colonies proved to express the gE protein. Of these four colonies, 3T3 gE clone 9 was used to isolate a subclone having a high gE expression. The clone isolated by this method (called 3T3gE 9.5) was used for characterizing candidate anti-gE monoclonal antibodies.

5) Eukaryotic expression of both the BHV-1 glycoprotein gE and the BHV-1 glycoprotein gI in the same cell To express the BHV-1 glycoprotein gI in the same cell as the BHV-1 glycoprotein gE we first determined the putative position of the BHV-1 gI gene. Because the herpes simplex virus glycoprotein gI gene is located just upstream of the glycoprotein gE gene, it was inferred that the BHV-1 gI gene would be located on a corresponding position. To test this, the sequence has been determined of a region of 283 nucleotides, located about 1 kb upstream of the start of the BHV-1 gE gene. Conceptual translation of this region showed that the second reading frame codes for a 94 amino acids sequence that is homologous to the herpes simplex virus glycoprotein gI (FIGS. 13 and 14). Because the homologous segment is about 80 amino acids from the start codon the putative start of the open reading frame of the BHV-1 gI gene is estimated about 250 nt upstream from the sequenced region. From this it was inferred that the 1.7 kb SmaI fragment that starts 400 nt upstream from the sequenced region and ends within the gE gene should contain the complete coding region of the BHV-1 gI gene. This 1.7 kb SmaI fragment has been cloned into the eukaryotic vector MSV-neo (See FIG. 15). This vector contains the strong Murine Sarcoma Virus promoter and the selector gene neo that codes for the resistance against the antibiotic G-418 sulphate Geneticin. The resulting construct MSV-neoGI has been amplified in *E. coli* DH5α cells and has been transfected into 3T3gE 9.5 cells using the method of Graham and Van der Eb. The transfected cells were selected with 400 μg Geneticin/ml culture medium and the resistant colonies have been isolated and tested with candidate anti-gE Mabs that failed to react with 3T3gE 9.5 cells. From this we selected the 3T3gE/gI R20 clone that reacted with e.g. Mab 66 as well as wild type BHV-1 does.

6) Characterization of candidate anti-gE Mabs

Mabs were produced against wild-type BHV-1 and selected for their inability to react with Difivac-1 infected embryonic bovine trachea (Ebtr) cells. These Mabs are examined for their reactivity with a) the Lam $gE^-$deletion mutant;

b) the above described prokaryotic expression product in a Western blot;

c) the above described gE-expressing Balb/c-3T3 cells;

d) cells mentioned under c) and infected with Difivac-1, and e) Balb/c-3T3 cells expressing the gE/gI complex.

For reactivity testing under a, c, d and e and immunoperoxidase monolayer assay (IPMA) was used. The results in Table 2 show that we have produced Mabs that are directed against gE/nrs. 2, 3, 4, 52, 66, 68, 72 and 81) and Mabs (nrs. 1, 51, 53, 67, 75 and 78) that may be directed against conformational antigenic domains on the gE/gI complex. A competition IPMA to map the antigenic domains recognized by the various Mabs indicated that at least 4 antigenic domains are present on glycoprotein gE and that one domain probably is formed by the gE/gI complex (Table 2).

Detection of anti-gE antibodies in cattle infected by BHV-1

To examine whether in serum of infected cattle antibodies against gE are present an indirect blocking IPMA was performed with the 16 candidate gE/Mabs and the following 8 selected sera:

2sera of bovines vaccinated with Difivac-1 and challenged with the virulent Iowa strain, that were collected 14 days after challenge;

2 sera of bovines experimentally infected with BHV-1 subtype 1 virus, that were collected 20 months after infection. One of the bovines was infected by contact exposure;

2 sera of bovines experimentally infected with BHV-1 subtype 2b virus, that were collected 20 months after infection. One of the bovines was infected by contact exposure;

a serum of a specific pathogen free calf vaccinated with a ts mutant vaccine and challenged 3 weeks later with BHV-1 subtype 2b virus, that was collected 7 weeks after challenge;

a serum of a gnotobiotic calf vaccinated with a ts mutant vaccine and challenged 3 weeks later with BHV-1 subtype 2B virus, that was collected 7 weeks after challenge.

Table 2 shows that all these sera contained antibodies against the antigenic domains III and IV or gE, and against antigenic domain I that is probably located on the gE/gI complex. We may conclude that gE appears to be a suitable serological marker to distinguish between BHV-1-infected and vaccinated cattle.

7) Detection of BHV-1 nucleic acids by means of the PCR procedure using BHV-1 gE-specific primers Starting from the determined nucleotide sequence of the BHV-1 gE gene, a primer pair suitable for the PCR was selected, using the primer selection program by Lowe et al. (T. Lowe, J. Sharefkin, S. Qi Yang and C. W. Dieffenbach, 1990, Nucleic Acids Res. 18, 1757–1761). These primers were called $P_3$ and $P_4$ and are shown in FIG. 10. The primers are located 159nt apart and lead to the amplification of a fragment of 200 nt. Using primers $P_3$ and $P_4$ and isolated BHV-1 DNA, the conditions for the PCR procedure were optimized. This involved in particular the variation of the MgCl$_2$ concentration, the glycerol concentration and the cycling conditions. The optimum buffer found for the use of P$_3$ and P$_4$ for the amplification of BHV-1 DNA is 10 mM Tris pH 8.0, 50 mM KCl, 0.01% gelatin, 2.6 mM MgCl$_2$ and 20% glycerol. The optimum cyclic conditions found (Perkin Elber Cetus DNA Thermal Cycler) are for cycli 1–5: 1 min. 98° C. 30 sec. 55° C. and 45 sec. 72° C. and for cycli 6–35: 30 sec. 96° C., 30 sec. 55° C. and 45 sec. 72° C. After the PCR amplification, the 200 nt DNA fragment obtained was electrophoresed on a 2% agarose gel, blotted on nitrocellulose and subsequently subjected to Southern blot analysis. The $^{32}$P dCTP labeled probe used for the Southern blot analysis is the 137 bp TaqI fragment which is located between the primer binding sites (FIG. 10). After autoradiography of the hybridized filters, a 200 bp band can be observed. Via this route, amplification of only 10 BHV-1 genomes (approx. 1.5×10$^{-15}$ µg DNA) still leads to a properly detectable signal (result not shown). In a comparable manner, a PCR procedure was developed using primers which are based on the coding sequence of the BHV-1 glycoprotein gIII (D. R. Fitzpatrick, L. A. Bubiuk and T. Zamb, 1989, Virology 173, 46–57). To enable a distinction to be made between wild-type BHV-1 DNA and a gE deletion mutant vaccine, DNA samples were subjected both to the gE-specific PCR and to gIII-specific PCR analysis. In such a test, a Difivac-1 DNA preparation was found to be gIII positive and gE negative. Because the detection of BHV-1 DNA in bovine semen will be an important use of the BHV-1 specific PCR procedure, it was attempted to perform the gE-specific PCR on bovine semen infected with BHV-1. However, unknown components in the semen have a strongly inhibitory effect on the polymerase chain reaction. Therefore, a protocol was developed to isolate the BHV-1 DNA from bovine semen. To isolate the DNA from bovine semen, 30 µl of semen is incubated with 1 mg/ml proteinase K (pK) in a total volume of 300µl 0.15M NaCl, 0.5% Na-Sarkosyl and 40 mM DTT, at 60° C. After 1 hour the sample is allowed to cool down to room temperature and 300 µl 6M NaI is added and incubated for 5 min. From this mixture DNA is isolated with a standard chloroform/isoamylethanol extraction and precipitated with 1 volume isopropanol. The precipitate is washed with 2.5 M NH$_4$Ac/70% ethanol and resuspended in 10 mM Tris pH7.4, 1 mM EDTA, 0.5% Tween 80 and 0.1 mg/ml pK for a second incubation for 1 hour at 60° C. This DNA preparation can be directly submitted to the Polymerase Chain Reaction.

Southern blot analysis of BHV-1 strains Difivac-1 and Iowa

Figure 1A:
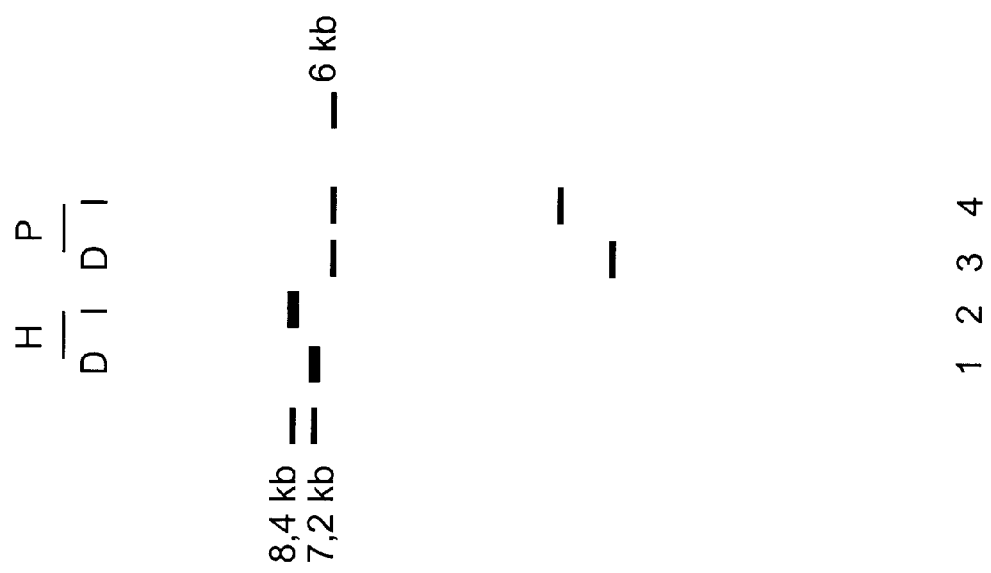
FIGS. 1A and 1B.

FIG. 1A. Drawing of an autoradiogram of a southern blot of Difivac-1 and Iowa genomic DNA. In lanes 1 and 3, Difivac-1 DNA was applied after restriction enzyme digestion with HindIII and PstI, respectively. In lanes 2 and 4, Iowa DNA was applied after restriction enzyme digestion with HindIII and PstI, respectively. The size of the fragments is indicated in kilobase (kb).

Viral DNA was isolated by centrifuging the culture medium (70 ml/roller bottle of ca. 450 cm$^2$) with virus infected Ebtr cells for 2 h through a 25% (w/w) sucrose cushion, in 10 mM Tris pH 7.4, 150 mM NaCl and 1 mM EDTA at 20 krpm in the SW27 rotor of the Beckman L5-65 ultracentrifuge. From the virus pellet so obtained, DNA was isolated according to standard methods (J. Sambrook, E. F. Fritsch and T. Maniatis, 1989, Molecular cloning: a laboratory manual, 2nd ed. Cold Spring Harbor Laboratory Press, New York). On this DNA, restriction enzyme digestions were performed with enzymes from Boehringer Mannheim in the SuRE/cut buffers supplied by the manufacturer.

After separation on a 0.7% agarose gel for horizontal electrophoresis and blotting on a nitrocellulose filter (Schleicher & Schuell, Inc.) the filter was prehybridized for 6 h at 42° C. in 50% formamide, 3x SSC (1x SSC=0.15M NaCl and 0.015 M Na-citrate, pH 7.4), 50 µl denatured salmon sperm DNA (Sigma)/ml and 0.02% bovine serum albumin, 0.02% polyvinyl pyrrolidone and 0.02% ficoll and 0.1% Na-dodecylsulphate (SDS). Then, hybridization was performed by adding to the same solution the $^{32}$P dCTP (Amersham) labeled HindIII K fragment (The choice of the HindIII K fragment is based on: Cloning and cleavage site mapping of DNA from bovine herpesvirus 1 (Cooper strain), John F. Mayfield, Pater J. Good, Holly J. VanOort, Alphonso R. Campbell and David A. Reed, Journal of Virology (1983) 259–264). After 12–14 h hybridization, the filter was washed for 2 h in 0.1% SDS and 0.1xSSC at 60° C. The HindIII K fragment was cloned into the pUC18 vector according to standard cloning procedures (J. Sambrook, E. F. Fritsch and T. Maniatis, 1989, Molecular cloning: a laboratory manual, 2nd ed. Cold Spring Harbor Laboratory Press, New York). After HindIII digestion of the pUC/8.4 HindIIIK clone the pUC18 vector was separated from the 8.4 kb HindIII K fragment again by electrophoresis on a 0.7% Low Melting Point Agarose (BRL, Life Technologies, Inc.) gel, and isolated from the agarose by standard phenol extraction and ethanol precipitation. The isolated HindIII K fragment was labeled with the Random Primed DNA labeling Kit 1004.760 from Boehringer Mannheim. Autoradiography of the hybridized filters was carried out through 36 h exposition of a Kodak XAR film at −70° C., using a reflecting screen.

Figure 1B:
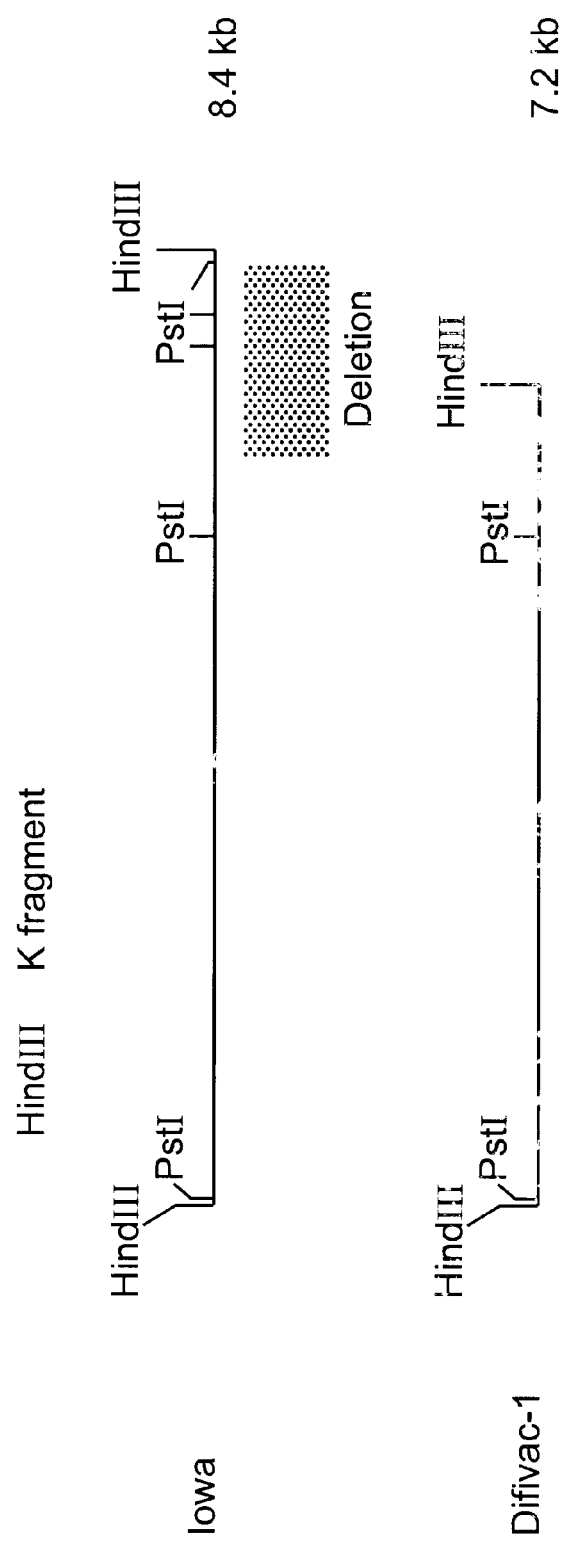

FIG. 1B. Physical maps of the 8.4 kb HindIII K fragment of Iowa and of the 7.4 kb HindIII fragment of Difivac-1. In view of the comigration of the 6 kb PstI fragments and the absence of the 1.8 kb PstI fragment in Difivac-1, the deletion is postulated in the hatched area.

FIG. 2

Subcloning of wild-type BHV-1 fragments around the region lacking in Difivac-1

In A the components of the BHV-1 genome are shown: The Unique Long (U$_L$) region; the Unique Short (U$_S$) region and the two repeats (Ir and Tr). This map is based on the published analysis of the Cooper strain (John F. Mayfield, Peter J. Good, Holly J. VanOort, Alphonso R. Campbell and David A. Reed, Journal of Virology (1983) 259–264).

In B the fragments are shown from the U$_S$ region which have been cloned into prokaryotic vectors: A 15.2 kb EcoRI fragment in pACYC, an 8.4 kb HindIII fragment in pUC18 and a 2.7 kb and a 4.1 kb EcoRI-HindIII fragment in pBR322. The isolation of the viral DNA fragments was carried out according to the procedures which are mentioned in the legends of FIG. 1A. The cloning of these fragments into the various vectors was carried out according to standard procedures (J. Sambrook, E. F. Fritsch and T. Maniatis, 1989, Molecular cloning: a laboratory manual, 2nd ed. Cold Spring Harbor Laboratory Press, New York).

In C a physical map is shown of the region where the postulated deletion in Difivac-1 is localized.

In D some subclones of this region are indicated, which were used for further analysis. The two PstI fragments were cloned into pKUN19 and the remaining fragments into pUC18.

Figure 2:
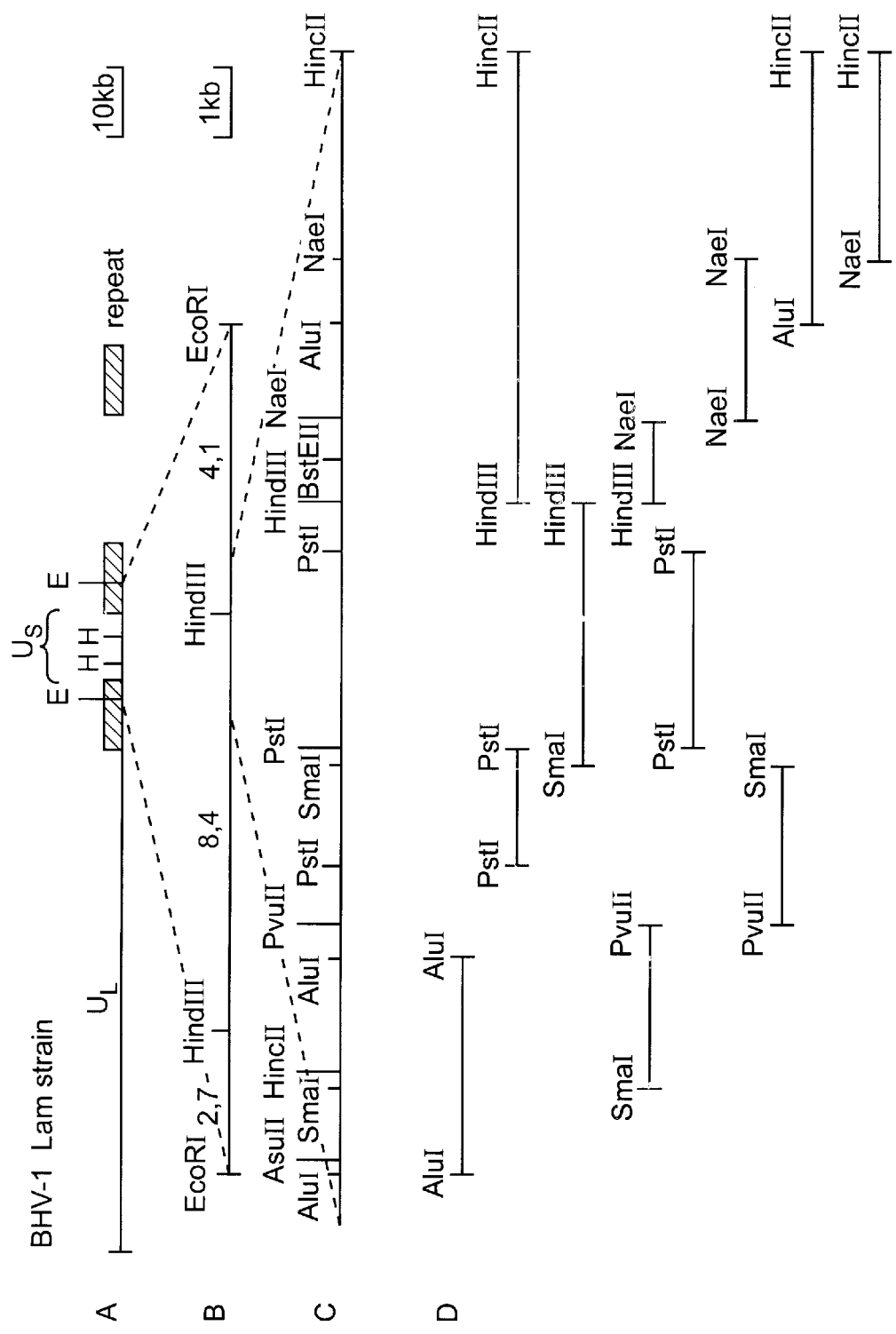
Figure 3B:
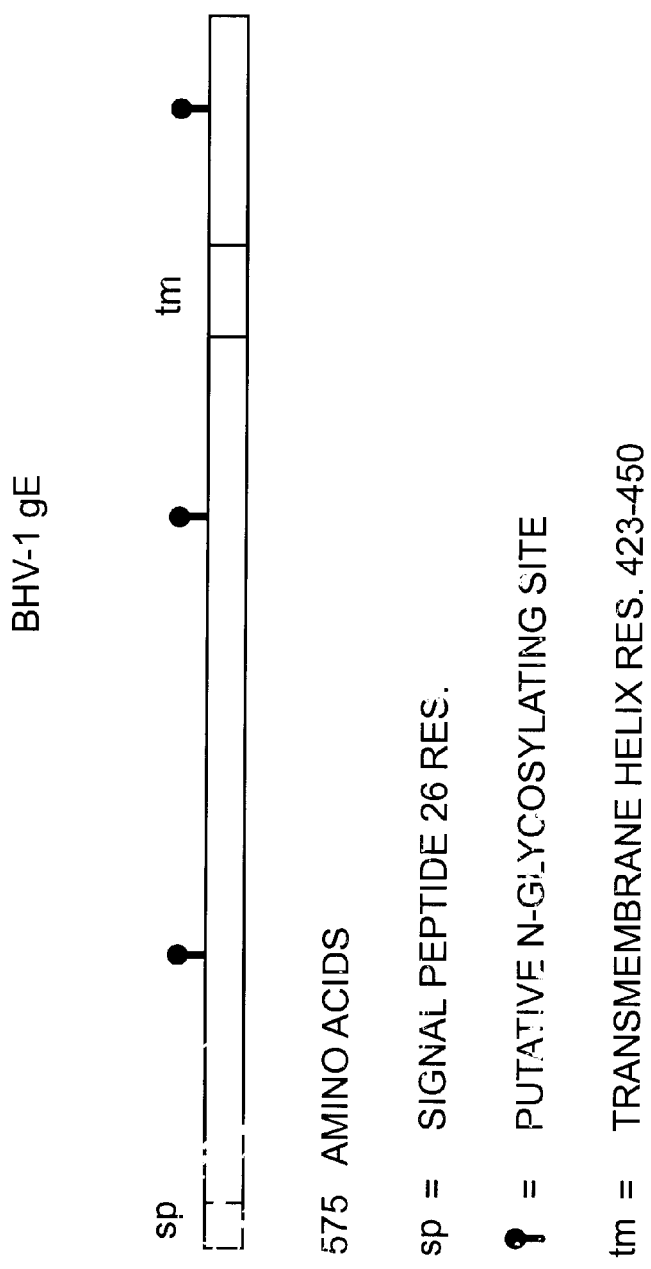

FIGS. 3A and 3B:

FIGS. 3A-1 to 3A-6 SEQ ID NO:1. Nucleotide sequence of 2027 nucleotides from the $U_S$ region of BHV-1 strain Lam around the postulated location which has been deleted in Difivac-1, as indicated in FIG. 2C [from the AluI recognition site on the extreme left to the HincII recognition site on the extreme right]. The nucleotide sequence in the inserts of the subclones shown in FIG. 2D was determined by analyzing on the two strands using the dideoxy sequence method of Sanger et al. (F. Sanger, S. Nicklen and A. R. Coulson, 1977, Proc. Natl. Acad. Sci. USA 74, 5463–5467). To that end, the T7 sequence kit of Pharmacia was used according to the procedure specified by the manufacturer. For the radioactive labeling, [$^{35}$S] dATP (Amersham) was used. The sequence analysis of the GC rich regions with compression artefacts was repeated with the 7-deaza-dGTP variant of the Pharmacia kit. Indicated beneath the nucleotide sequence is, in the three-letter code, the amino acid (aa) sequence of the open reading frame of 575 aa residues, which was found after conceptual translation of the nucleotide sequence. This translation is based on the universal code and was determined using the PC/gene computer program (PC/gene version 1.03, November 1987). This open reading frame of 575 aa starts with the methionine at nt 168 and ends with the stop codon at nucleotide 1893.

Structural analysis of the open reading frame of 575 aa residues was also performed with the PC/gene computer program. The first 26 aa form a eukaryotic export signal indicated in the figure by "signal peptide". With a score of 6.2, the cleavage of this signal sequence is predicted between aa 26 and aa 27. The sequence of 575 aa has 3 possible N-bound glycosylation sites (NXT/S) indicated by a line under the amino acid residues. According to the Rao and Argos method there is a transmembrane region between aa 423 and aa 450 indicated in the figure by "transmembrane helix". Recognition sequences (sites) for the restriction enzymes AsuII, SmaI, HindIII and EcoNI are underlined. The calculated molecular weight of this polypeptide is 61212.

FIG. 3B: Schematic representation of the structural characteristics of the above mentioned 575 aa open reading frame.

FIGS. 4A–4B

Amino acid comparison of the amino acid sequence of the BHV-1 gE gene with the amino acid sequence of the herpes simplex virus (HSV) gE gene and other gE homologous genes [pseudo-rabies virus (PRV) gI and varicella-zoster (VZV) gpI].

The sequences used for this comparison come from the following publications; HSV: Sequence determination and genetic content of the short unique region in the genome of herpes simplex virus type 1. D. J. McGeoch, A. Dolan, S. Donald and F. J. Rixon (1985) Journal Mol. Biol. 181, 1–13. VZV: DNA sequence of the $U_S$ component of the varicella-zoster virus genome. A. J. Davidson (1983), EMBO Journal 2, 2203–2209. PRV: Use of λgt11 to isolate genes for two pseudorabies virus glycoproteins with homology to herpes simplex virus and varicella-zoster virus glycoproteins. E. A. Petrovskis, J. G. Timmins and L. E. Post (1986) Journal of Virology 60, 185–193]. These sequences were compared using the sequence analysis program Multalin (F. Corpet, 1988, Nucl. Acids Res. 16, 10881–10890).

Figure 4A:
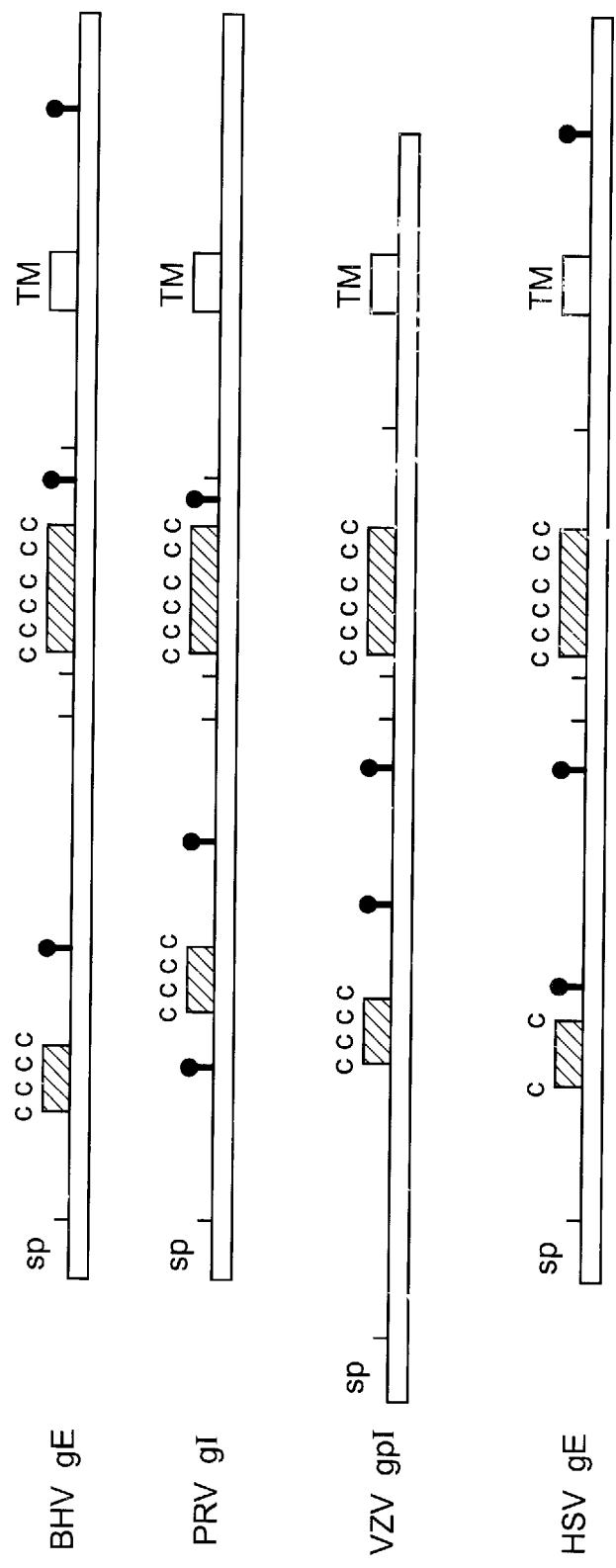
Figure 5:
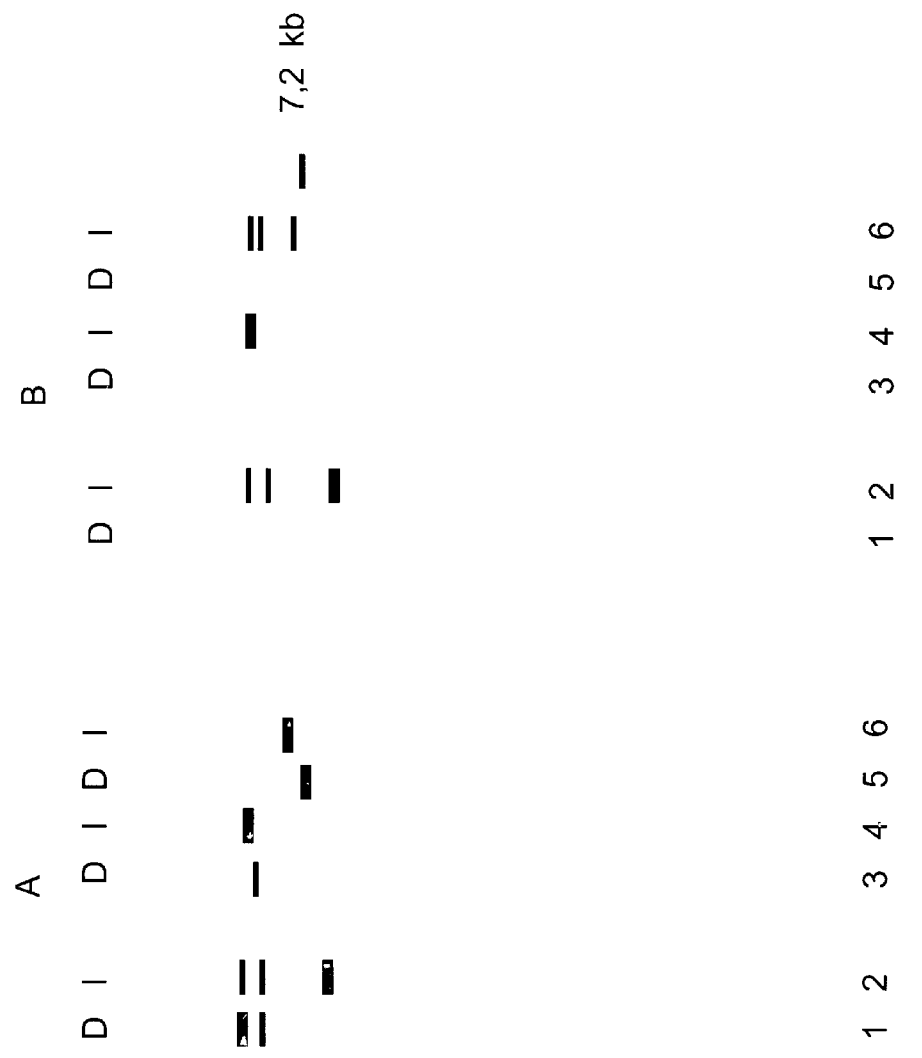
Figure 6:
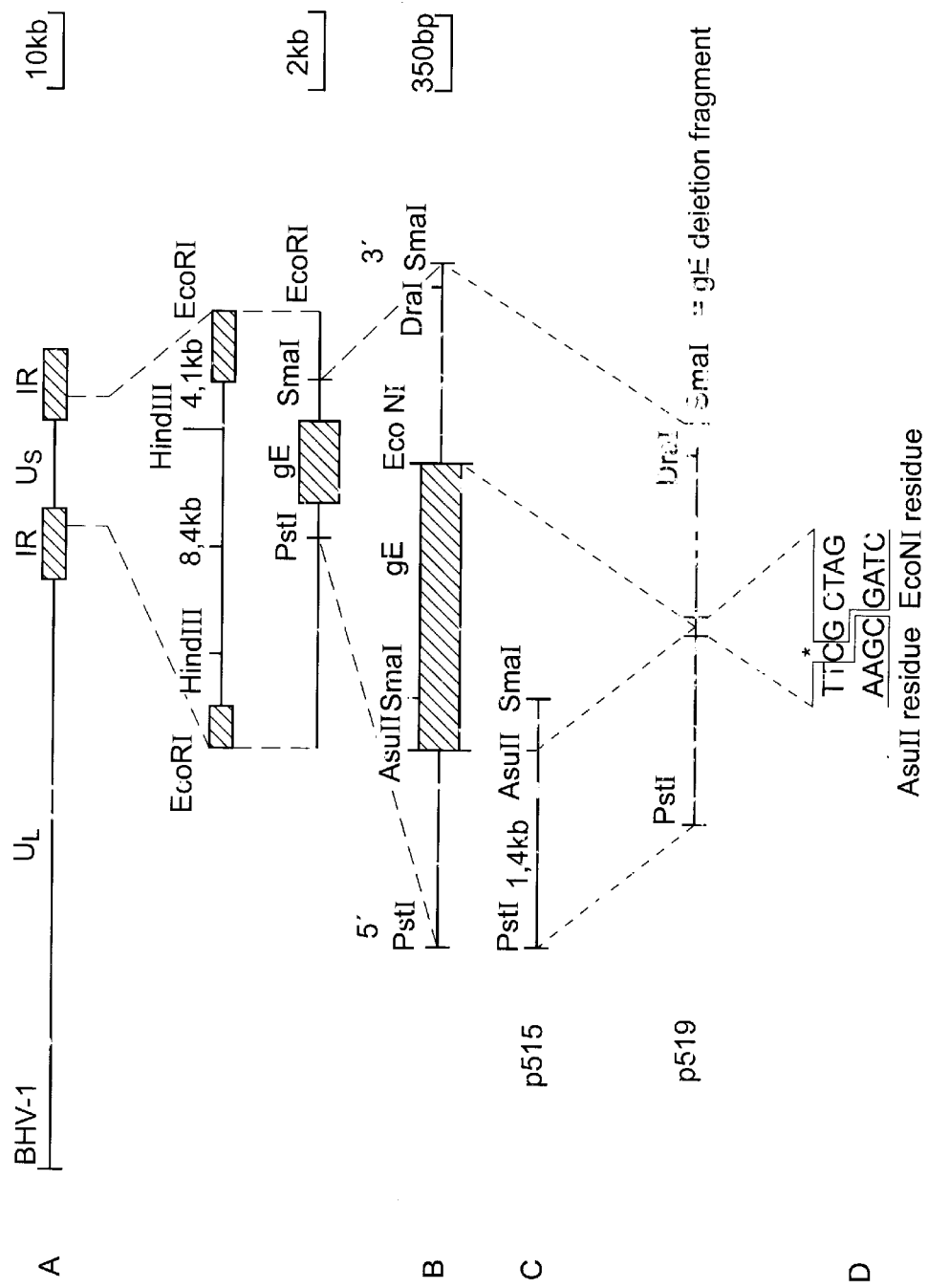

In FIG. 4A a diagram is shown in which all four amino acid sequences are shown schematically. Here, the predicted transmembrane parts (TM) are shown below each other. In addition to the predicted export signal sequences (SP) and the possible N-bound glycosylation sites (I), two conserved areas are shown, in which the relative position of the cysteine residues is often unchanged (C C C).

In FIG. 4B SEQ ID NO:7 to SEQ ID NO:14 the results are shown of the Multalin comparison of the centrally located cysteine rich region of the four gE versions. Asterisks indicate identical amino acids and colons analogous amino acids.

FIG. 5

Drawing of photographs obtained in a Southern blot analysis of Difivac-1 and Iowa Panel A: Genomic DNA of Difivac-1 and Iowa restriction enzyme digestions with BstI (1,2), EcoRI (3,4) and HindIII (5,6) separated on a 0.7% agarose gel, blotted on nitrocellulose and hybridized with $^{32}$P labeled HindIII K fragment of BHV-1 strain Lam according to the procedures specified in the legends of FIG. 1A.

Panel B: Nitrocellulose blot of the same gel as in A hybridized with the BHV-1 gE-specific probe p318. This probe comprises the entire AluI-HincII region indicated in FIG. 2C.

FIG. 6

Construction of gE deletion fragment BHV-1

In A the position of the gE gene and the clones used is shown. The components of the BHV-1 genome are: The unique Long ($U_L$) region; the Unique Short ($U_S$) region and the two repeats (IR and TR). To obtain the region located on the 5' side of the gE gene, the 1.4 kb PstI-SmaI fragment from the 8.4 kb HindIII K fragment of BHV-1 strain Lam was subcloned into the SmaI and PstI site of a plasmid pUC18. This clone was called p515 and is shown in B. The EcoNI-SmaI fragment located on the 3' side of gE, coming from the 4.1 kb HindIII-EcoRI clone was cloned into the unique AsuII site of p515. To enable the ligation of the EcoNI rest to the AsuII rest, clone p515 was digested with AsuII, then treated with Klenow enzyme (Boehringer Mannheim) and dCTP to provide one cytosine residue in the AsuII rest according to standard methods (Sambrook et al., 1989). This additional cytosine is indicated by an asterisk in D. Then, p515 was also digested with the SmaI enzyme, whereafter the EcoNI fragment could be ligated into this vector. The clone thus constructed was called p519.

FIGS. 7A–7B

Figure 7A:
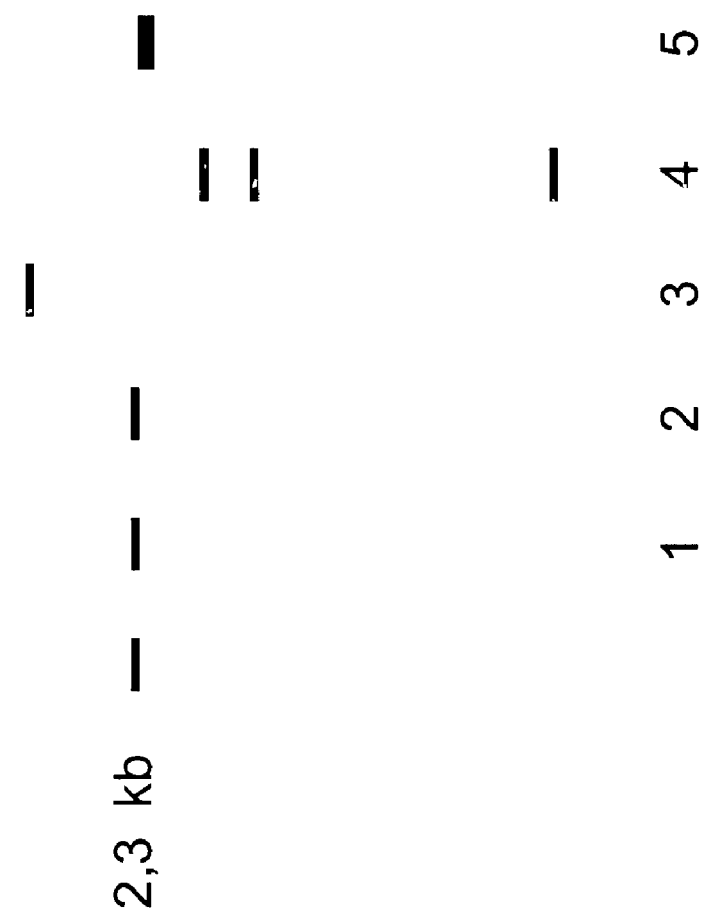

FIG. 7A. Drawing of a photograph obtained in Southern blot analysis of DNA preparations of 1B7, 1B8 and 2H10. DNA isolation, restriction enzyme digestions, blotting and hybridization were performed according to the procedures described in the legends of FIG. 1A. After PstI-DraI double digestion of the DNA preparations 1B7, 1B8 and 2H10, the fragments were separated on a 0.7% agarose gel and subsequently blotted on a nitrocellulose filter. This filter was hybridized with the $^{32}$P dCTP labeled 2.3 kb PstI-DraI deletion fragment as probe. In lanes 1 through 3, the samples 1B7, 1B8 and 2H10 were separated, respectively. In lane 4, wild-type BHV-1 DNA of the Lam strain was applied and in lane 5 the 2.3 kb deletion fragment.

Figure 7B:
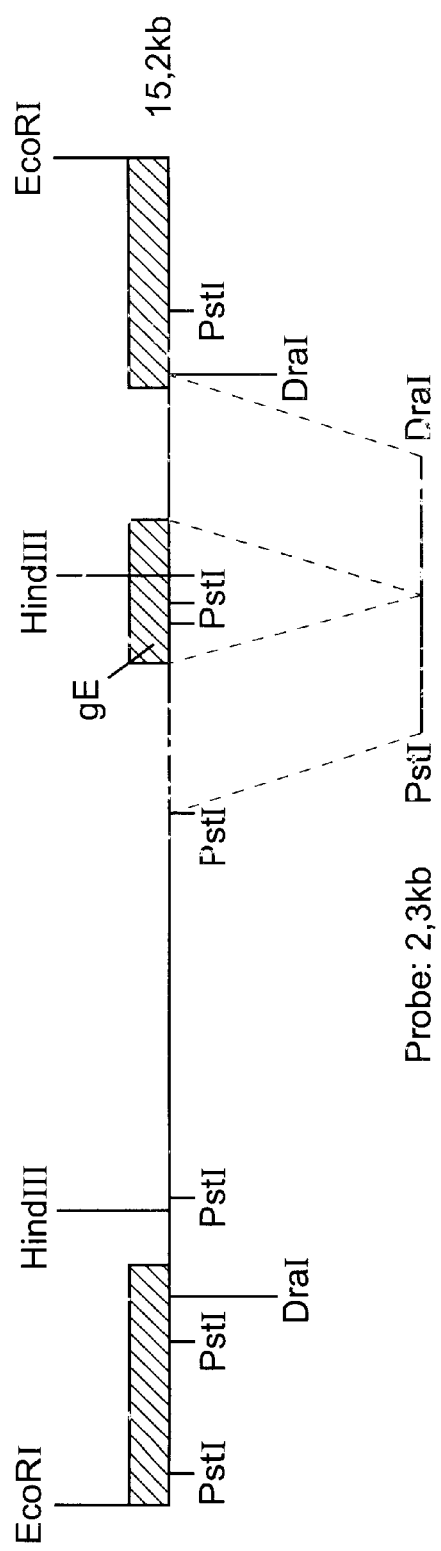
Figure 8A:
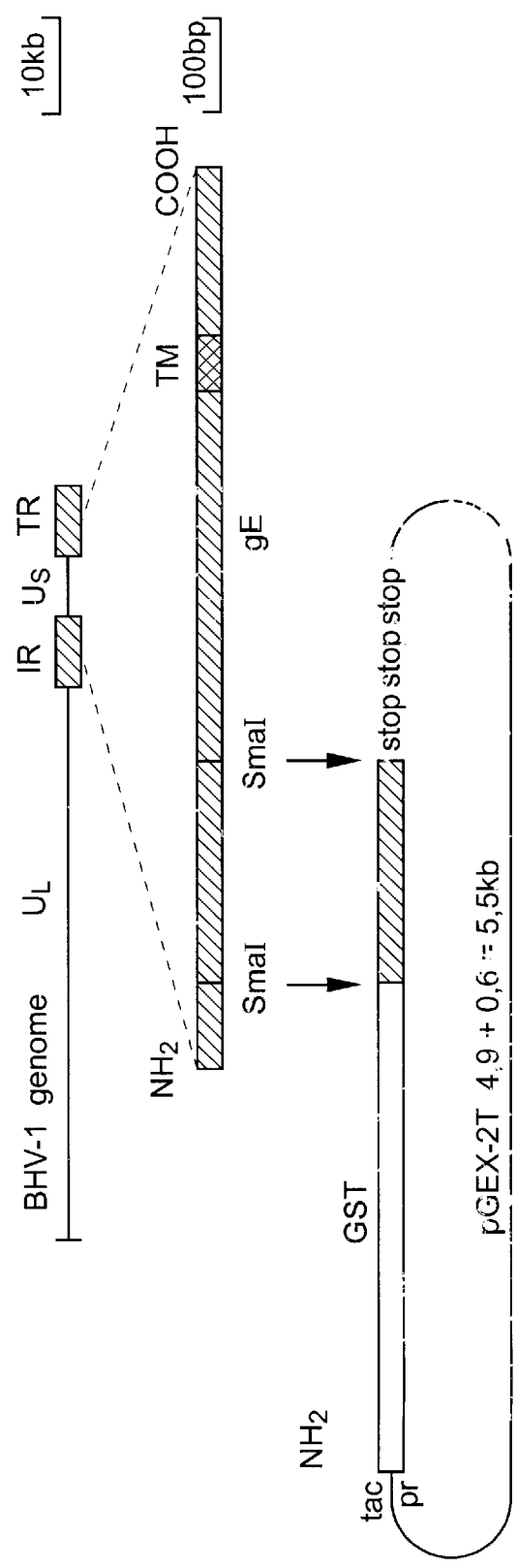
Figure 8B:
Figure 9:
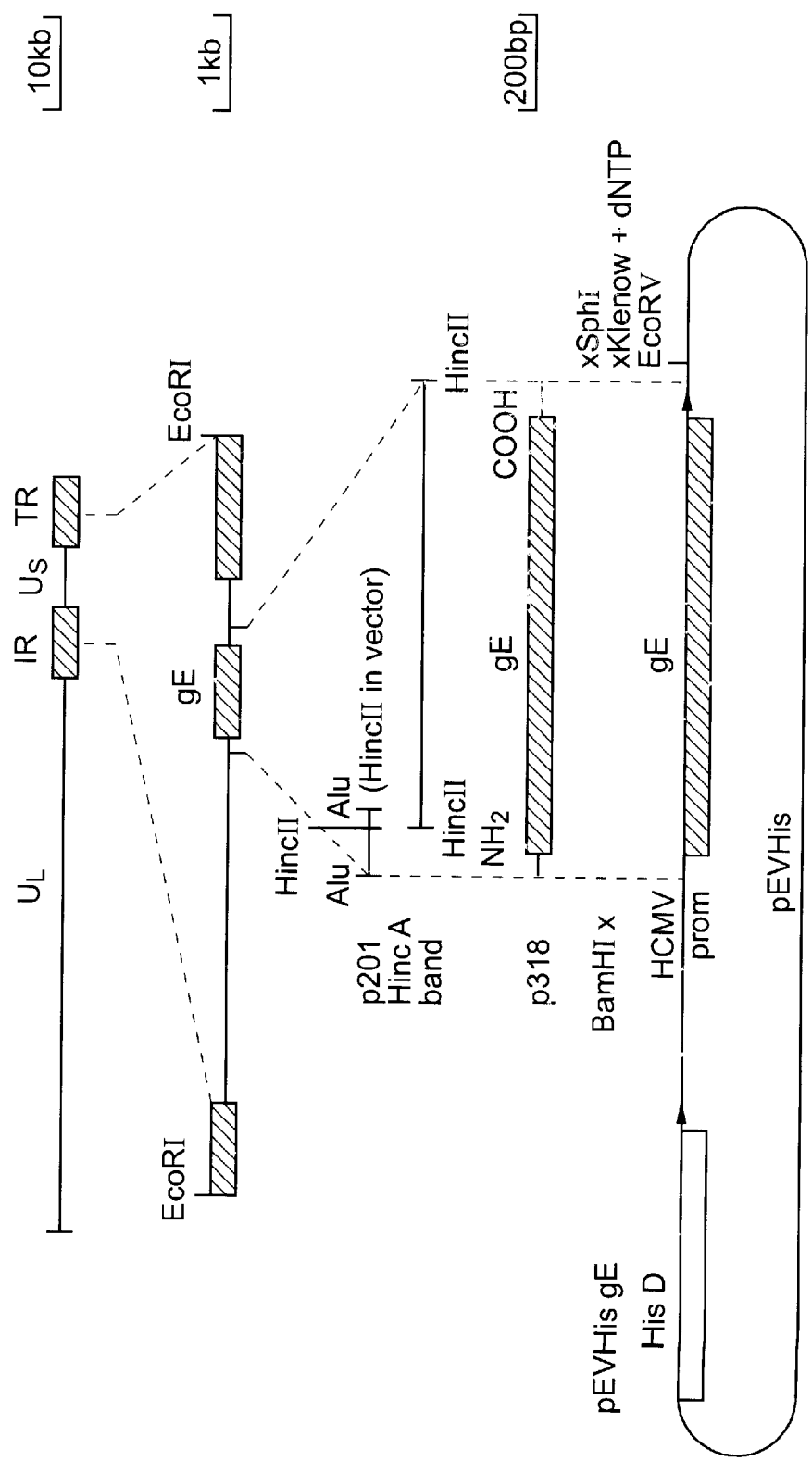

FIG. 7B. Physical map of the 15.2 kb EcoRI fragment of BHV-1 strain Lam. The map shows the position of the PstI, DraI and HindIII recognition sites and the position of the hybridization probe mentioned in 7A.

FIGS. 8A–8B

Prokaryotic expression of BHV-1 gE

Figure 11:
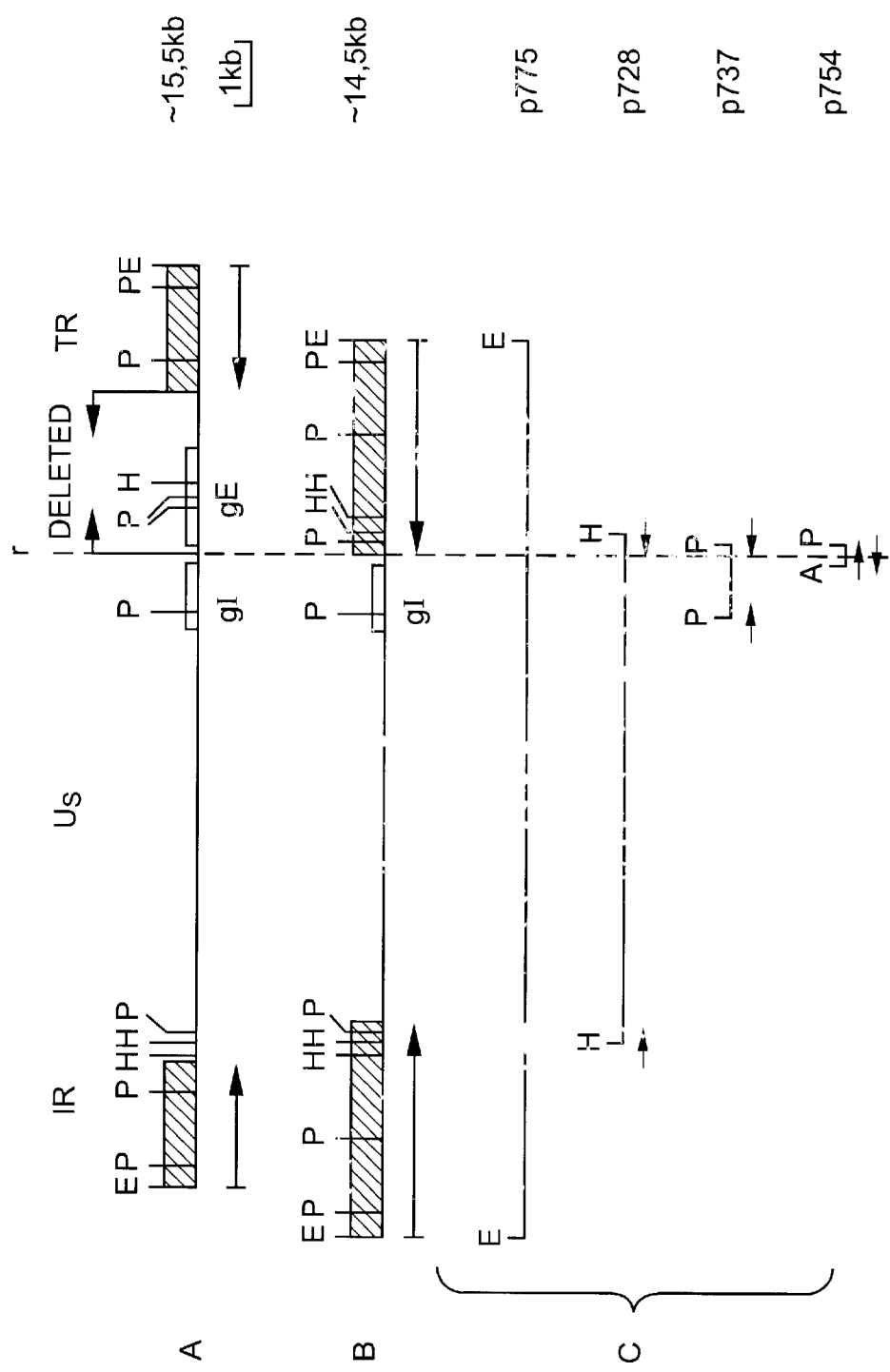
Figure 15:
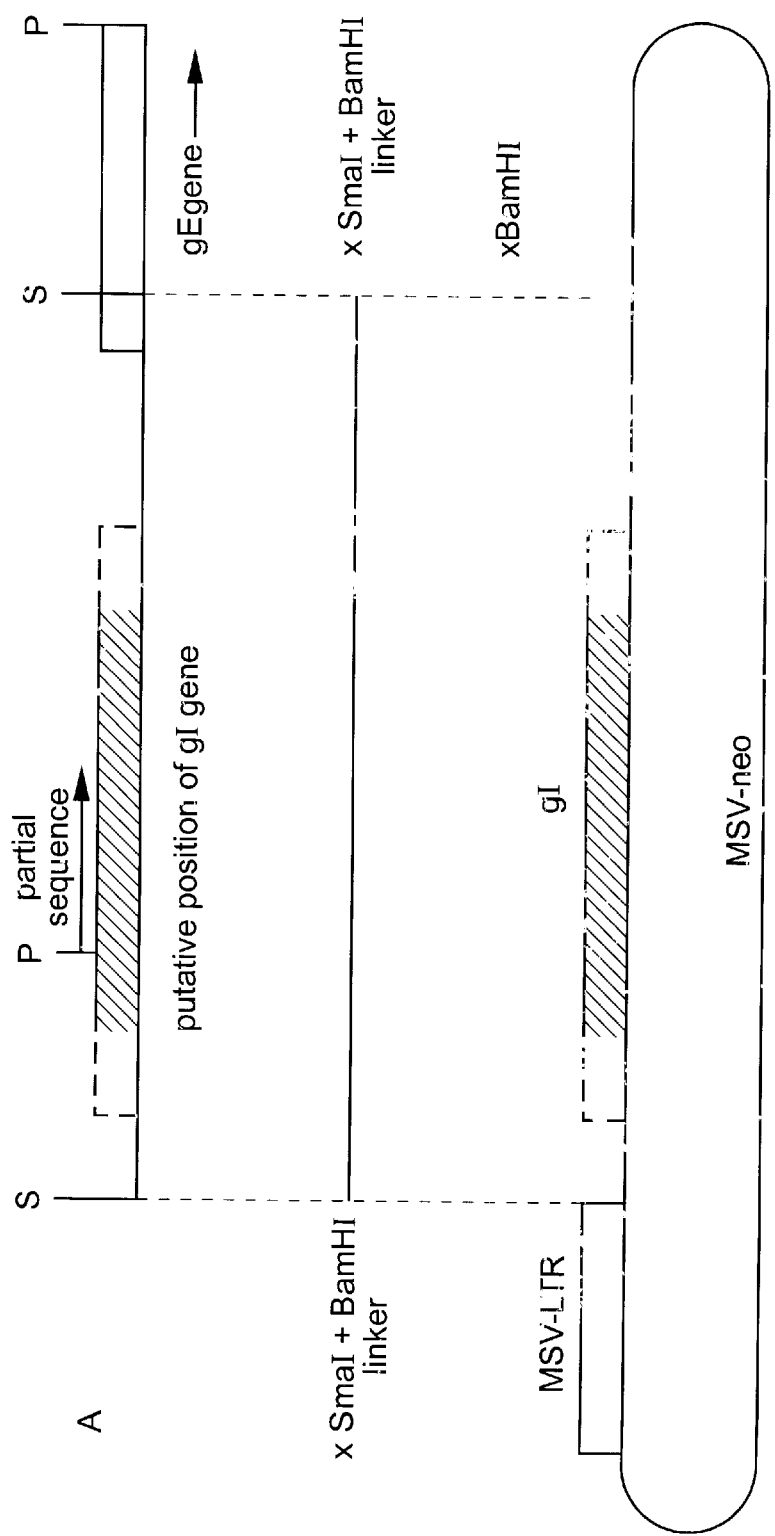
Figure 16:
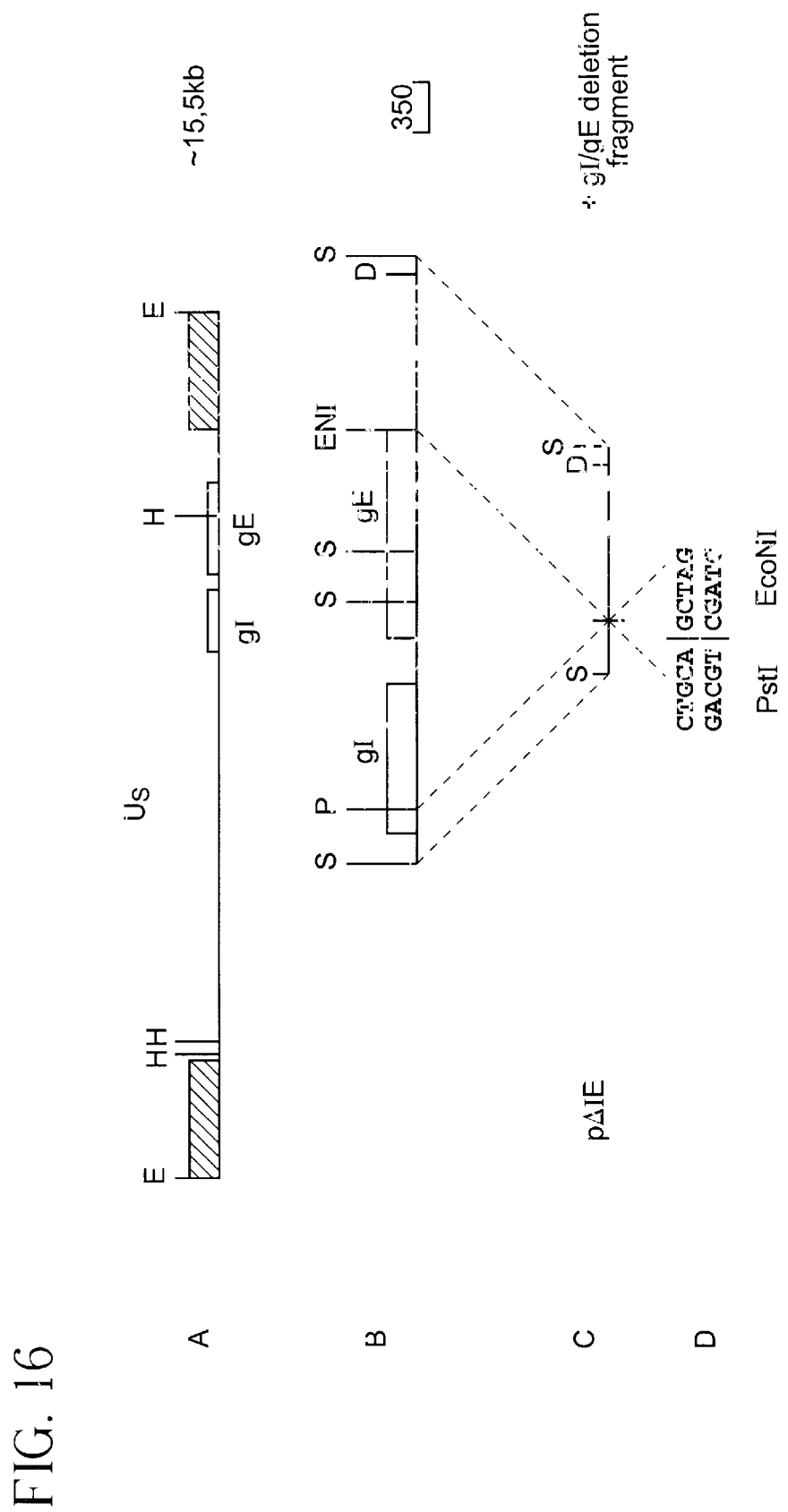
Figure 17:
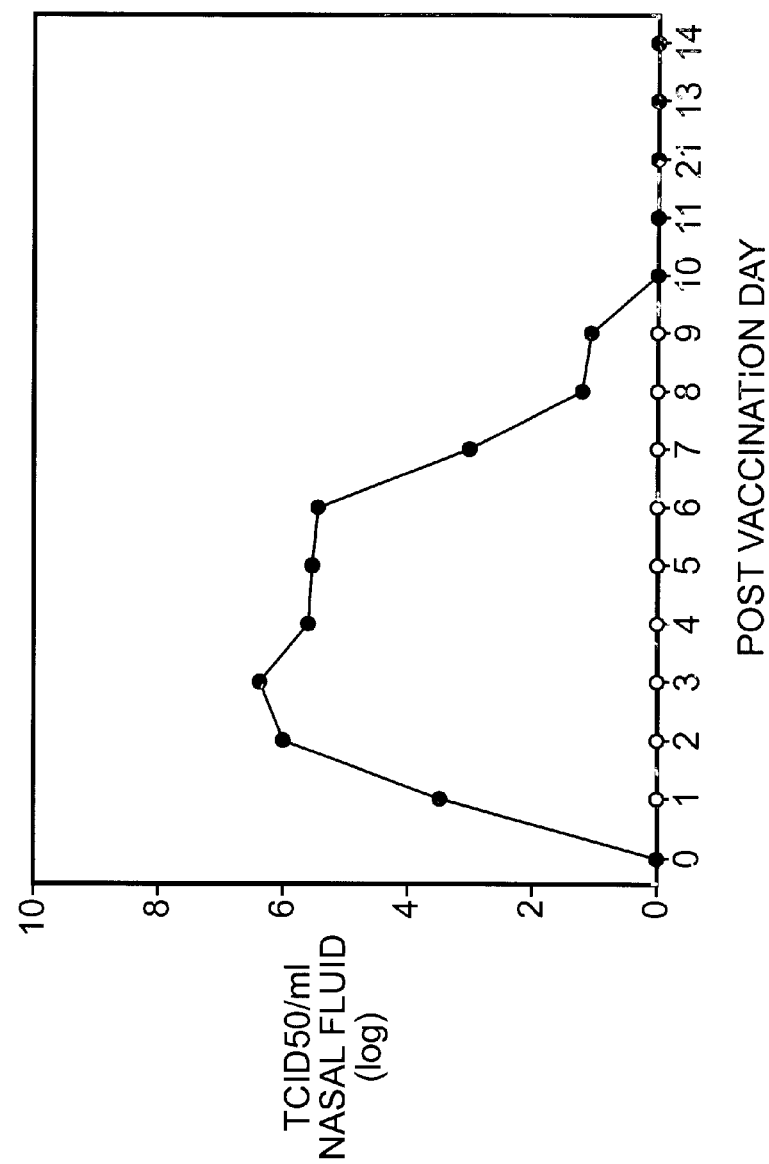
Figure 18:
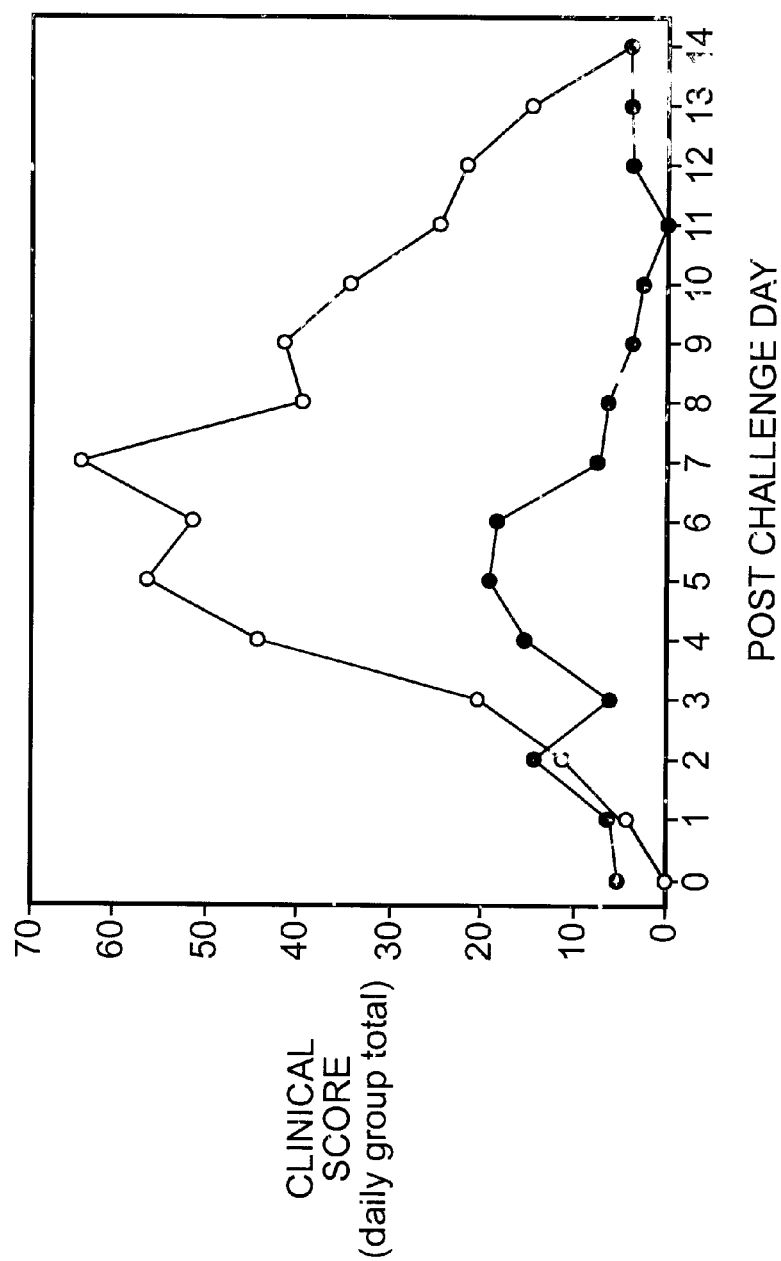
Figure 19:
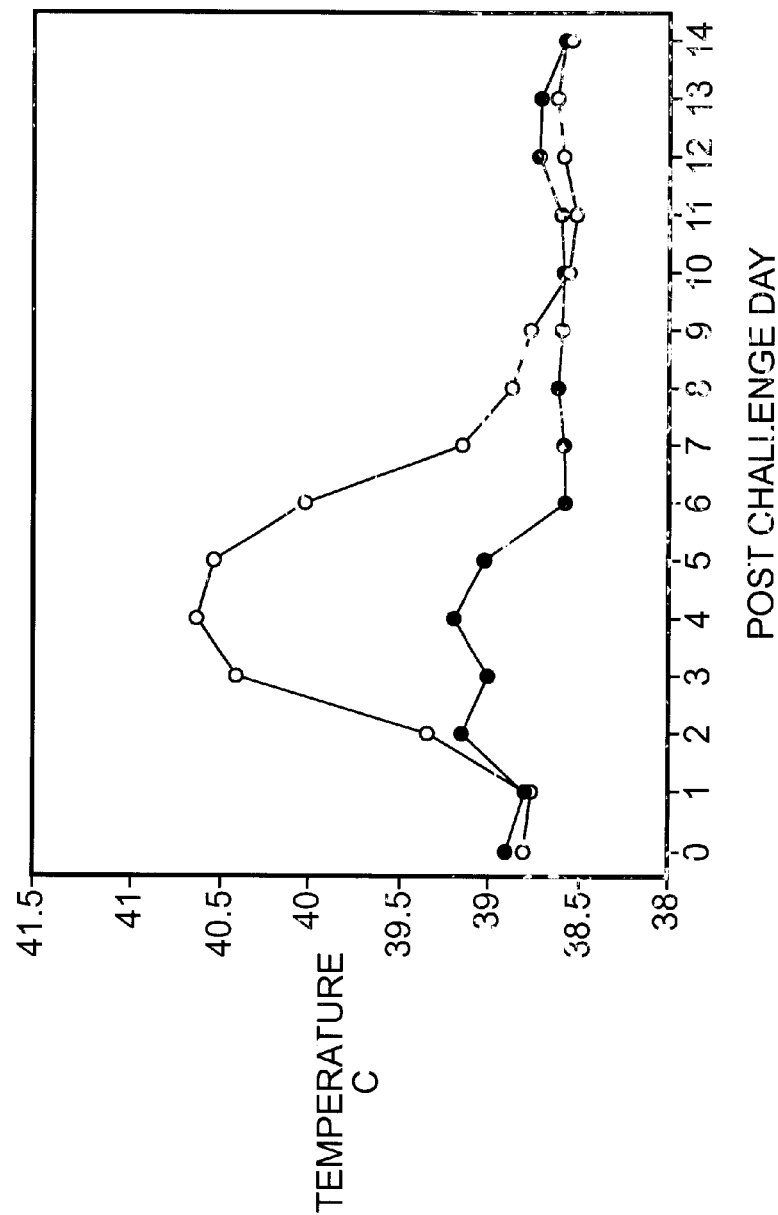
Figure 20:
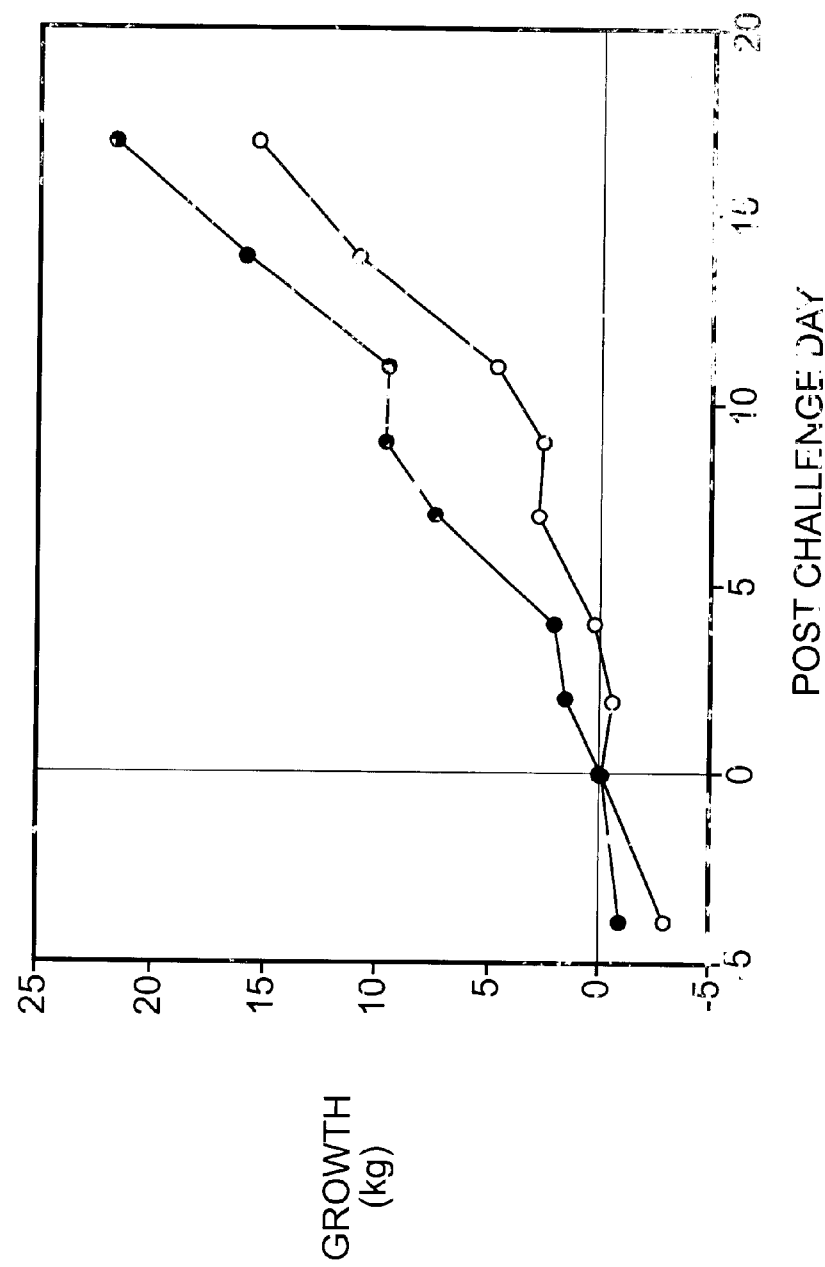
Figure 21:
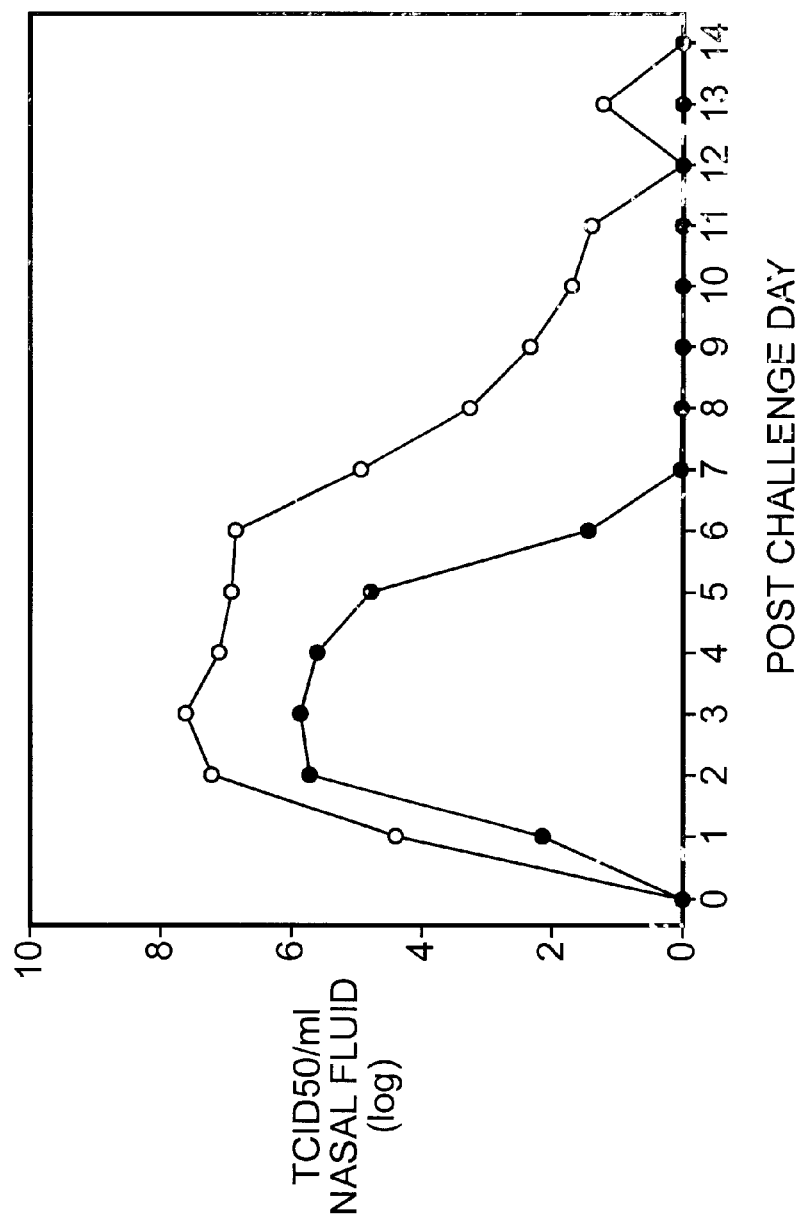
Figure 22:
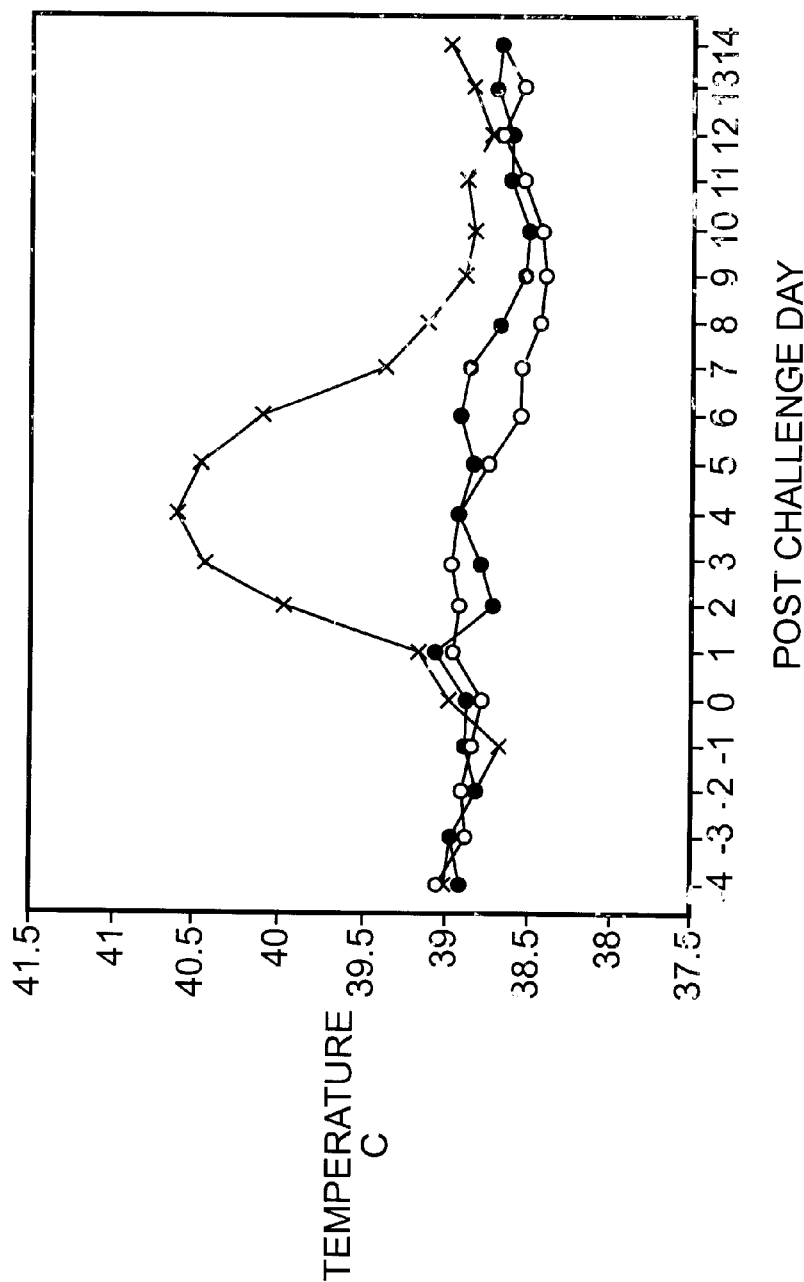
Figure 23:
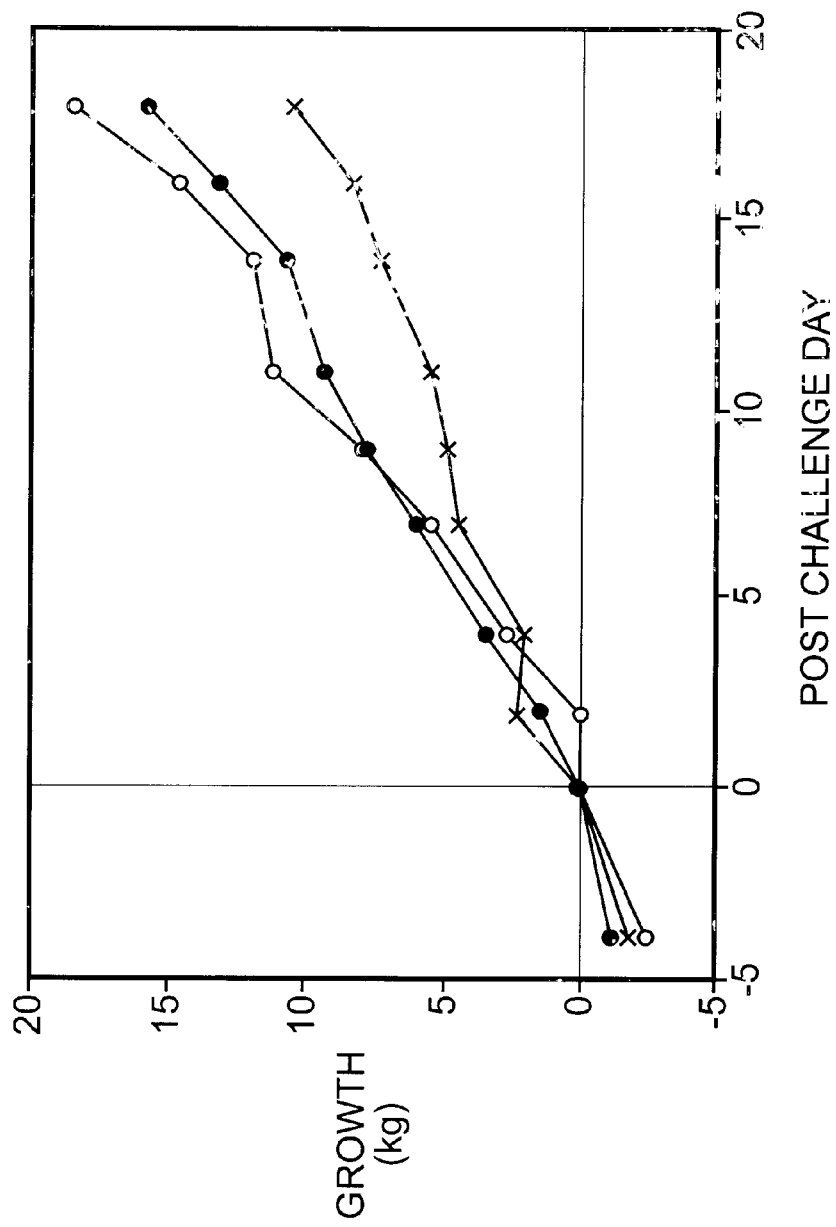
Figure 24:
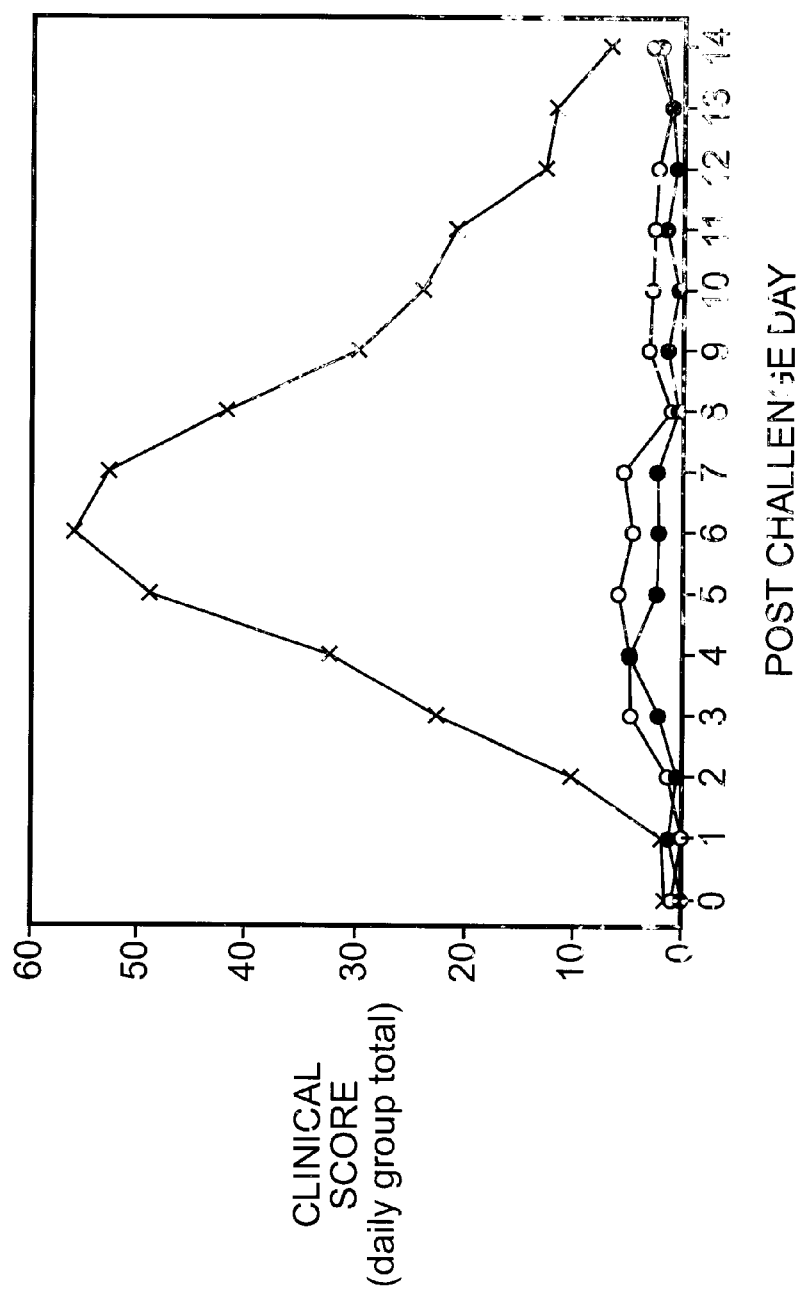

For the prokaryotic expression of BHV-1 gE, the 600 bp SmaI fragment of the gE gene was fused in three reading frames to the coding region of the glutathione-S-transferase gene from Schistosoma japonicum in the vector pGEX-2T (D. B. Smith and K. S. Johnson, Gene 67 (1988) 31–40). Recombinant molecules with the proper (syn) orientation of the SmaI fragment were identified by means of restriction enzyme analysis using standard methods. *E. coli* DH5α clones with this fusion construct were called pGEX-2T600s1, pGEX-2T600s2 and pGEX-2T600S3.

FIG. 8A. Diagram of one of the pGEX-2T600s constructs. Located on the $NH_2$ side of the region which codes for GST-gE fusion product is the Isopropylthiogalactoside (IPTG) inducible tac promoter region.

FIG. 8B. Drawing of photographs obtained in Western blot analysis of total protein preparations of DH5α cells transformed with pGEX-2T600s. Overnight cultures of DH5α cells transfected with the constructs pGEX-2T600s1, pGEX-2T600s2 and pGEX-2T600s3 were continued 1/10 in Luria-Bertani (LB) medium with 50 μg/ml ampicillin and after 1 h growth induced with IPTG for 5 h. These induced cultures were centrifuged for 5 min at 6,000 x g and incorporated in 1 x layermix (2% SDS, 10% Glycerol, 5% mercaptoethanol and 0.01% bromophenol blue) [1.5 ml culture is incorporated in 500 μl layermix] and heated at 95° C. for 5 min. Then 50 μl per lane was separated on a vertical 12.5 % polyacrylamide gel according to standard procedures and subsequently Semi-dry blotted to a nitrocellulose filter using the LKB-multiphor II Nova Blot system under the conditions specified by the manufacturer.

In lanes M, prestained marker protein was applied (BRL Life Technologies, Inc. 236 k, 112 k, 71 k, 44 k, 28 k, 18 k and 15 k) and in lanes 1, 2 and 3 the total protein preparations of DH5α cells transfected with the three respective frames: pGEX-2T600s1, pGEX-2T600s2 and pGEX-2T 600S3.

In panel A, the result can be seen of the western blot analysis with anti-GST serum. To that end, the filter was incubated according to standard procedures (E. Harlow and D. Lane, 1988, Antibodies: a laboratory manual, Cold Spring Harbor Laboratory, New York) in blocking buffer (PBS+2% milk powder and 0.05% Tween 20) and subsequently with polyclonal anti-GST rabbit serum. Then the filter was washed and incubated with horse radish peroxidase (HRPO) conjugated goat-anti-rabbit immunoglobulin serum. Then the bound goat antibodies were immunochemically detected with chromogen (diaminobenzidine, chloronaphthol and $H_2O_2$). The GST fusion product which is indicated by an arrow has the predicted size of approx. 47 k only in frame 3.

In panel B, the result can be seen of the western blot analysis with monoclonol antibody Mab 4, which recognizes the gE protein. To that end, a duplo filter as in panel A was blocked, incubated with Mab, washed, and incubated with HRPO conjugated rabbit-anti-mouse serum. Then, the bound rabbit antibodies were immunochemically detected with chromogen. The band which is visible in lane 3 (frame 3) is 47 k in size and is indicated by an arrow.

FIG. 9

Construction of the pEVHisgE plasmid for the eukaryotic expression of the BHV-1 gE gene For the eukaryotic expression of the gE gene, the entire gE coding region was cloned in the proper orientation behind the HCMV promoter region of the expression vector pEVHis using standard procedures (Sambrook et al. 1989). To that end, the 394 bp AluI fragment which starts 55 bp before the open reading frame of the gE was cloned into pUC18 and called p201. Then, after HincII digestion of p201, the 1740 bp HincII fragment, which comprises the greater part of the gE gene was cloned into p201. This resulted in the plasmid p318which in the polylinker of pUC18 comprises the entire gE coding area from the AluI site 55 bp before the start codon of gE to the HincII site 133 bp behind the stop codon of gE. Using the restriction enzyme sites in the polylinker of the vector, this fragment was cut from p 318 with the enzymes BamHI and SphI. First, p318 was digested with SphI and then the SphI site was filled in using Klenow polymerase and dNTP's. After the digestion with BamHI, the 1.9 kb insert was separated from the pUC18 vector in Low Melting Point Agarose and ligated in the pEVHis vector which had been digested with BamHI and EcoRV to that end. The plasmid so formed was called pEVHis/gE.

FIG. 10

Position of the gE-specific primers and probe for the PCR procedure for detecting BHV-1 DNA Shown in the figure is the nucleic acid sequence of the BHV-1 glycoprotein gE gene from nucleotide 1272 to 2027 [the sequence has been taken over from FIGS. 3A-1 to 3A-6]. The primers used for the gE-specific PCR procedure were called $P_3$ and $P_4$. The primer binding sites for $P_3$ and $P_4$ are underlined. The nucleotide sequence of $P_3$ is 5'-ACG-TGG-TGG-TGC-CAG-TTA-GC-3' (SEQ ID NO:15). The nucleotide sequence of $p_4$ is (complementary to the primer binding sequence specified above) 5'-ACC-AAA-CTT-TGA-ACC-CAG-AGC-G-3' (SEQ ID NO:16). The probe which was used for the Southern blot hybridization for the detection of the PCR amplified DNA, is the 137 bp TaqI fragment located between the primer binding sites, the ends of this fragment being indicated. For comparison with FIG. 3, the HindIII and the EcoNI sites are also indicated.

FIG. 11

Mapping of the gE deletion of Difivac-1

A shows the physical map of the 15.5 kb EcoRI fragment of the wild type BHV-1 strain Lam. B shows the physical map of the 14.5 kb EcoRI fragment of Difivac-1. Both EcoRI fragments cover the complete Unique short regions of the genomes of the respective viruses. The position of the gE gene and the putative position of the gI gene have been indicated by open boxes. Maps A and B are positioned in such a way, that the 6 kb PstI fragments within each map are aligned. In both maps the internal repeat and the terminal repeat sequences have been indicated by hatched boxes. The arrows beneath the repeats indicate the orientation of these sequences.

In A the part of the $U_S$ region that is missing in the Difivac-1 strain has been indicated.

C shows the position of the cloned Difivac-1 fragments used to map the gE deletion and to obtain the physical map shown in B. The arrows beneath the inserts of clones p728, p737 and p754 indicate the regions that have been sequenced to determine the recombination point.

Abbreviations:

A=AluI, E=EcoRI, P=PstI. H=HindIII, r=recombination point, IR=internal repeat, TR=terminal repeat.

FIG. 12

Determination of the exact recombination point in the $U_S$ region of Difivac-1

To determine the exact borders of the gE deletion found in the Difivac-1 strain, clone p754 and the ends of clones p728 and p737 have been sequenced. The inserts of these clones have been indicated in FIG. 11. The sequence procedures used have been described in the legends of FIG. 3.

In A SEQ ID NO:11 the sequence of most of the AluI-PstI fragment has been shown. This sequence starts in the promoter region of the gE gene. A putative TATA box has been underlined. At point r (=recombination point) this promoter region is fused to a sequence also found at the opposite site of the $U_S$ region, named: inverted repeat. The exact recombination point has been determined by comparing the repeat found at the gE promoter region with the copy of the repeat found at the opposite site of the $U_S$ region. The point were these sequences diverge has been indicated in B (under I) with 'r'. A similar comparison has been made with the gE promoter sequence found in Difivac-1 and the gE promoter found in wild type strain Lam. The point were these sequences diverge has been shown in B (under II) and also indicated with 'r'. The recombination points found are the same.

FIG. 13

Partial sequence analysis of the BHV-1 gI gene

Using the 1.8 kb PstI clone of BHV1 strain Lam, that reaches into both the BHV-1 gI and gE gene (See FIG. 11), the sequence of 284 nucleotides within the coding region of BHV-1 gI was determined SEQ ID NO:2. The sequence procedures used have been described in the legends of FIG. 3A. The sequence has been translated based on the universal code by the PC/gene computer program version 1.03 (November 1987). The amino acid sequence encoded by the second reading frame is given in the one letter code beneath the nucleotide sequence. This amino acid sequence is homologous to the coding region of other herpes virus gI homologs (see FIG. 14 SEQ ID NO:3 to SEQ ID NO:6).

FIG. 14

Amino acid comparison of the partial amino acid sequence of the putative BHV-1 gI gene SEQ ID NO:3 with the corresponding parts of the coding regions of the herpes simplex virus (HSV1) gI gene SEQ ID NO:5, the pseudorabies virus (PRV) gp63 SEQ ID NO:4 and the varicella-zoster virus (VZV) gpIV gene SEQ ID NO:6.

The PRV sequence SEQ ID NO:4 starts at amino acid 82, the HSV1 sequence starts at aa 80 SEQ ID NO:5 and the VZV sequence starts at aa 76 SEQ ID NO:6 of their respective coding regions. The sequences used were published in the papers mentioned in the legends of FIG. 4. The comparison was performed using the Multalin computer program. Asterisks indicate identical amino acids and colons indicate analogous amino acids.

FIG. 15

Construction of the MSVneoGI plasmid for the eukaryotic expression of the BHV-1 gI gene Based on the amino acid comparison of the partial sequence of the BHV-1 gI gene, the putative position of the BHV-1 gI gene has been estimated. Based on this estimation it was inferred that the 1.7 kb SmaI fragment should contain the complete coding region of the BHV-1 gE gene. The position of this 1.7 kb SmaI fragment has been indicated in A. To the blunt ends of this 1.7 kb SmaI fragment, BamHI linkers have been ligated, using standard procedures. The resulting product was digested with BamHI and ligated into the eukaryotic expression vector MSV-neo. The MSV-neo vector has a unique BamHI site behind the MSV-LTR, which has a strong promoter activity. This vector has been described in Rijsewijk et al., 1987 EMBO J. 6, 127–131.

FIG. 16

Construction of a BHV-1 gI/gE double deletion fragment

The position of the glycoprotein gE gene and the putative position of the glycoprotein gI gene in the $U_S$ region of BHV-1 are depicted in diagram A. The hatched blocks indicate the repeats that border the $U_S$ region. B shows the physical map of some essential restriction enzyme sites with respect to the position of both genes. To construct the gI/gE deletion fragment clone P1.7-SmaI/o containing the 1.7 kb SmaI fragment that embraces the gI gene will be digested with PstI. The PstI site of the remaining 350 bp SmaI-PstI insert will be made blunt ended using standard molecular biological procedures. The EcoNI-SmaI fragment (see FIG. 6), isolated from the 4.1 kb HindIII-EcoRI fragment described in FIG. 6A, will also be made blunt ended and ligated to the modified PstI site. This is diagrammed in C and D. From the resulting clone pΔIE the 1.4 kb SmaI-DraI fragment can be isolated to recombine with wild type BHV-1 DNA.

Abbreviations:

E=EcoRI, H=HindIII, S=SmaI, P=PstI, ENI=EcoNI, D=DraI, kb=kilobase and $U_S$=unique short.

FIG. 17

Mean nasal virus shedding from calves after vaccination .=vaccinated with Difivac-1, 0=unvaccinated control.

FIG. 18

Mean daily clinical score of calves after challenge with a virulent BHV-1 strain, key as in FIG. 17.

FIG. 19

Mean rectal temperature of calves challenge with a virulent BHV-1 strain, key as in FIG. 17.

FIG. 20

Mean growth of calves after challenge with a virulent BHV-1 strain, key as in FIG. 17.

FIG. 21

Mean nasal virus shedding from calves after challenge with a virulent BHV-1 strain, key as in FIG. 17.

FIG. 22

Mean rectal temperature of calves after challenge with a virulent BHV-1 strain

.=vaccinated with Lam $gE^-$, 0=vaccinated with Lam $gE^-$/$TK^-$, x=unvaccinated control.

FIG. 23

Mean growth of calves after challenge with a virulent BHV-1 strain, key as in FIG. 22.

FIG. 24

Mean daily clinical score of calves after challenge with a virulent BHV-1 strain, key as in FIG. 22.

TABLE 1

Nasal virus shedding of calves after vaccination with Lam gE- or Lam $gE^-/TK^-$ and after challenge with a virulent BHV-1 strain of these vaccinated and control calves

| Group | Average number of days of nasal virus shedding After vaccination | After challenge |
|---|---|---|
| Control | 0 | 10.33 ± 1.51 |
| Lam $gE^-$ | 7.00 ± 0.89 | 4.83 ± 1.17 |
| Lam $gE^-/TK^-$ | 7.17 ± 1.33 | 5.17 ± 0.98 |

TABLE 2

Characterization of gE-Mabs

REACTIVITY OF CANDIDATE gE-Mabs WITH

| Mab | Difi-vac-1 3T3/ EBTR | Lam gE⁻ | Prok. | 3T3 gE | 3T3 gE Difi-vac-1 | 3T3 gE/gI | Ag group | Ab cattle |
|---|---|---|---|---|---|---|---|---|
| 1  | − | − | nd | − | + | ? | I   | + |
| 2  | − | − | −  | + | + | + | II  | − |
| 3  | − | − | +  | + | + | + | ?   | − |
| 4  | − | − | +  | + | + | + | ?   | − |
| 42 | − | − | nd | − | − | ? | V?  | ± |
| 51 | − | − | nd | − | + | + | III | + |
| 52 | − | − | +  | + | + | + | ?   | − |
| 53 | − | − | nd | − | + | + | III | + |
| 59 | − | − | nd | − | − | + | III | + |
| 66 | − | − | nd | + | + | + | III | + |
| 67 | − | − | nd | − | + | + | III | + |
| 68 | − | − | −  | + | + | + | IV  | + |
| 72 | − | − | −  | + | + | + | V   | ± |
| 75 | − | − | nd | − | + | ? | I   | + |
| 78 | − | − | nd | − | + | ? | nd  | − |
| 81 | − | − | −  | + | + | + | II? | − |

+ All 8 tested sera score a blocking percentage of >50% in an indirect blocking IPMA.
± Sera score a blocking percentage of ±50%.
− Sera score a blocking percentage of <50%.

---

What is claimed is:

1. A mutant of bovine herpesvirus type 1 (BHV-1) having a deletion in the glycoprotein gE-gene, wherein said deletion allows the mutant to be distinguished serologically from wild-type BHV-1, and said deletion has been constructed by recombinant DNA techniques.

2. A BHV-1 mutant according to claim 1, said mutant comprising a 1B7 mutant having a Southern blot profile as shown in FIG. 7.

3. The BHV-1 mutant according to claim 2, which is 1B7.

4. A BHV-1 mutant according to claim 1 which is a double deletion mutant having a deletion in the gE-gene and a deletion in another gene, with the proviso that if said another gene is the thymidine kinase gene, said mutant further contains a deletion in an additional gene.

5. A mutant of bovine herpesvirus type 1 (BHV-1) having a deletion in the glycoprotein gE-gene, wherein said deletion allows the mutant to be distinguished serologically from wild-type BHV-1, which contains a heterologous gene introduced by recombinant DNA techniques.

6. A BHV-1 mutant according to claim 5, said heterologous gene being inserted at the location of the gE-gene and being under the control of regulatory sequences of the gE-gene or a heterologous gene, and optionally attached to the part of the gE-gene that codes for a signal peptide.

7. A BHV-1 mutant according to claim 5 which, in addition to a deletion in the gE-gene, has a deletion in the thymidine kinase gene, a deletion in the gI-gene, or both, said heterologous gene being inserted at the location of at least one of said deletions.

8. A BHV-1 mutant according to claim 5 which, in addition to a deletion in the gE-gene, has a deletion in the thymidine kinase gene, a deletion in the gI-gene, or both, said heterologous gene being inserted at the location of at least one of said deletions, with the proviso that in the case of mutant having a double deletion comprising a deletion in the gE-gene and a deletion in the thymidine kinase gene, said heterologous gene is not inserted at the location of the thymidine kinase gene.

9. A BHV-1 mutant according to claim 5 which, in addition to a deletion in the gE-gene, has a deletion in the thymidine kinase gene, a deletion in the gI-gene, or both, said heterologous gene being inserted at the location of at least one of said deletions, with the proviso that in the case of a mutant having a double deletion comprising a deletion in the gE-gene and a deletion in the thymidine kinase gene, at least two heterologous genes are inserted.

10. A BHV-1 mutant according to claim 5 wherein said heterologous gene codes for an immunogenic protein or peptide of another pathogen or codes for a cytokine.

11. A vaccine composition for a vaccination of animals to protect them against BHV-1, wherein the vaccine composition is a live or an inactivated vaccine comprising a BHV-1 mutant having a deletion in the glycoprotein gE-gene, wherein said deletion allows the mutant to be distinguished serologically from wild-type BHV-1, and a suitable carrier or adjuvant.

12. A vaccine composition for a vaccination of animals to protect them against a pathogen, wherein the vaccine composition is a live or an inactivated vaccine comprising a BHV-1 mutant having a deletion in the glycoprotein gE-gene, wherein said deletion allows the mutant to be distinguished serologically from wild-type BHV-1, and said mutant contains a heterologous gene which has been introduced by recombinant DNA techniques and codes for an immunogenic protein or peptide of the pathogen, and a suitable carrier or adjuvant.

13. A BHV-1 mutant having a deletion in the glycoprotein gE-gene, wherein said deletion allows said mutant to be distinguished from wild-type BHV-1 by a process of discriminating between BHV-1 viruses having an intact gE-gene and BHV-1 viruses having a deletion in the gE-gene, said process comprising the step of examining whether nucleic acid of the virus reacts with gE-specific probes or primers derived from the nucleotide sequence coding for gE.

* * * * *

UNITED STATES PATENT AND TRADEMARK OFFICE
CERTIFICATE OF CORRECTION

PATENT NO.     : 6,403,097 B1
DATED          : August 2, 2002
INVENTOR(S)    : Rijsewijk et al.

It is certified that error appears in the above-identified patent and that said Letters Patent is hereby corrected as shown below:

<u>Title page,</u>
Item [74], *Attorney, Agent, or Firm,* now reads "Hoffman & Baron, LLP", should read -- Hoffmann & Baron, LLP --;

<u>Column 5,</u>
Line 3, now reads "mil", should read -- milk --;

<u>Column 10,</u>
Line 39, now reads "approximately", should read -- approximated --;

<u>Column 11,</u>
Line 36, now reads "TCIF$_{50}$", should read -- TCID$_{50}$ --;

<u>Column 12,</u>
Line 62, now reads "cotransferred", should read -- cotransfected --;

<u>Column 16,</u>
Line 53, now reads "III, and IV or gE", should read -- III, and IV on gE --;

<u>Column 17,</u>
Line 23, now reads " Bubiuk", should read -- Babiuk --.

Signed and Sealed this

Twenty-seventh Day of May, 2003

JAMES E. ROGAN
*Director of the United States Patent and Trademark Office*

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
       (A) LENGTH: 2027 nucleotides
       (B) TYPE: nucleotide
       (C) STRANDEDNESS: single
       (D) TOPOLOGY: Linear (xi) SEQUENCE DESCRIPTION: SEQ ID NO:1:

```
AGGGCGGAGC GTTGAGCGGC CCGACCGCCG CCGGGTTGTT AAATGGGTCT        50

CGCGCGGCTC GTGGTTCCAC ACCGCCGGAG AACCAGCGCG AGCTTCGCTG       100

CGTGTGTCCC GCGAGCTGCG TTCCGGGGAA CGGCGCACGC GAGAGGGTTC       150

GAAAAGGGCA TTTGGCA                                          167

ATG CAA CCC ACC GCG CCG CCC CGG CGG CGG T TG CTG CCG CTG CTG CTG        215
Met Gln Pro Thr Ala Pro Pro Arg Arg Arg L eu Leu Pro Leu Leu Leu
 1               5                  10                  15

CCG CAG TTA TTG CTT TTC GGG CTG ATG GCC G AG GCC AAG CCC GCG ACC        263
Pro Gln Leu Leu Leu Phe Gly Leu Met Ala G lu Ala Lys Pro Ala Thr
             20                  25                  30

GAA ACC CCG GGC TCG GCT TCG GTC GAC ACG G TC TTC ACG GCG CGC GCT        311
Glu Thr Pro Gly Ser Ala Ser Val Asp Thr V al Phe Thr Ala Arg Ala
         35                  40                  45

GGC GCG CCC GTC TTT CTC CCA GGG CCC GCG G CG CGC CCG GAC GTG CGC        359
Gly Ala Pro Val Phe Leu Pro Gly Pro Ala A la Arg Pro Asp Val Arg
     50                  55                  60

GCC GTT CGC GGC TGG AGC GTC CTC GCG GGC G CC TGC TCG CCG CCC GTG        407
Ala Val Arg Gly Trp Ser Val Leu Ala Gly A la Cys Ser Pro Pro Val
```

-continued

```
                65                      70                      75                      80
CCG GAG CCC GTC TGC CTC GAC GAC CGC GAG T GC TTC ACC GAC GTG GCC             455
Pro Glu Pro Val Cys Leu Asp Asp Arg Glu C ys Phe Thr Asp Val Ala
                        85                      90                      95

CTG GAC GCG GCC TGC CTG CGA ACC GCC CGC G TG GCC CCG CTG GCC ATC             503
Leu Asp Ala Ala Cys Leu Arg Thr Ala Arg V al Ala Pro Leu Ala Ile
                        100                     105                     110

GCG GAG CTC GCC GAG CGG CCC GAC TCA ACG G GC GAC AAA GAG TTT GTT             551
Ala Glu Leu Ala Glu Arg Pro Asp Ser Thr G ly Asp Lys Glu Phe Val
                        115                     120                     125

CTC GCC GAC CCG CAC GTC TCG GCG CAG CTG G GT CGC AAC GCG ACC GGG             599
Leu Ala Asp Pro His Val Ser Ala Gln Leu G ly Arg Asn Ala Thr Gly
                        130                     135                     140

GTG CTG ATC GCG GCC GCA GCC GAG GAG GAC G GC GGC GTG TAC TTC CTG             647
Val Leu Ile Ala Ala Ala Ala Glu Glu Asp G ly Gly Val Tyr Phe Leu
145                     150                     155                     160

TAC GAC CGG CTC ATC GGC GAC GCC GGC GAC G AG GAG ACG CAG TTG GCG             695
Tyr Asp Arg Leu Ile Gly Asp Ala Gly Asp G lu Glu Thr Gln Leu Ala
                        165                     170                     175

CTG ACG CTG CAG GTC GCG ACG GCC GGC GCG C AG GGC GCC GCG CGG GAC             743
Leu Thr Leu Gln Val Ala Thr Ala Gly Ala G ln Gly Ala Ala Arg Asp
                        180                     185                     190

GAG GAG AGG GAA CCA GCG ACC GGG CCC ACC C CC GGC CCG CCG CCC CAC             791
Glu Glu Arg Glu Pro Ala Thr Gly Pro Thr P ro Gly Pro Pro Pro His
                        195                     200                     205

CGC ACG ACG ACA CGC GCG CCC CCG CGG CGG C AC GGC GCG CGC TTC CGC             839
Arg Thr Thr Thr Arg Ala Pro Pro Arg Arg H is Gly Ala Arg Phe Arg
210                     215                     220

GTG CTG CCG TAC CAC TCC CAC GTA TAC ACC C CG GGC GAT TCC TTT CTG             887
Val Leu Pro Tyr His Ser His Val Tyr Thr P ro Gly Asp Ser Phe Leu
225                     230                     235                     240

CTA TCG GTG CGT CTG CAG TCT GAG TTT TTC G AC GAG GCT CCC TTC TCG             935
Leu Ser Val Arg Leu Gln Ser Glu Phe Phe A sp Glu Ala Pro Phe Ser
                        245                     250                     255

GCC AGC ATC GAC TGG TAC TTC CTG CGG ACG G CC GGC GAC TGC GCG CTC             983
Ala Ser Ile Asp Trp Tyr Phe Leu Arg Thr A la Gly Asp Cys Ala Leu
                        260                     265                     270

ATC CGC ATA TAC GAG ACG TGC ATC TTC CAC C CC GAG GCA CCG GCC TGC            1031
Ile Arg Ile Tyr Glu Thr Cys Ile Phe His P ro Glu Ala Pro Ala Cys
                        275                     280                     285

CTG CAC CCC GCC GAC GCG CAG TGC AGC TTC G CG TCG CCG TAC CGC TCC            1079
Leu His Pro Ala Asp Ala Gln Cys Ser Phe A la Ser Pro Tyr Arg Ser
                        290                     295                     300

GAG ACC GTG TAC AGC CGG CTG TAC GAG CAG T GC CGC CCG GAC CCT GCC            1127
Glu Thr Val Tyr Ser Arg Leu Tyr Glu Gln C ys Arg Pro Asp Pro Ala
305                     310                     315                     320

GGT CGC TGG CCG CAC GAG TGC GAG GGC GCC G CG TAC GCG GCG CCC GTT            1175
Gly Arg Trp Pro His Glu Cys Glu Gly Ala A la Tyr Ala Ala Pro Val
                        325                     330                     335

GCG CAC CTG CGT CCC GCC AAT AAC AGC GTA G AC CTG GTC TTT GAC GAC            1223
Ala His Leu Arg Pro Ala Asn Asn Ser Val A sp Leu Val Phe Asp Asp
                        340                     345                     350

GCG CCG GCT GCG GCC TCC GGG CTT TAC GTC T TT GTG CTG CAG TAC AAC            1271
Ala Pro Ala Ala Ala Ser Gly Leu Tyr Val P he Val Leu Gln Tyr Asn
                        355                     360                     365

GGC CAC GTG GAA GCT TGG GAC TAC AGC CTA G TC GTT ACT TCG GAC CGT            1319
Gly His Val Glu Ala Trp Asp Tyr Ser Leu V al Val Thr Ser Asp Arg
                        370                     375                     380

TTG GTG CGC GCG GTC ACC GAC CAC ACG CGC C CC GAG GCC GCA GCC GCC            1367
```

```
Leu Val Arg Ala Val Thr Asp His Thr Arg Pro Glu Ala Ala Ala
385                 390                 395                 400

GAC GCT CCC GAG CCA GGC CCA CCG CTC ACC AGC GAG CCG GCG GGC GCG    1415
Asp Ala Pro Glu Pro Gly Pro Pro Leu Thr Ser Glu Pro Ala Gly Ala
                405                 410                 415

CCC ACC GGG CCC GCG CCC TGG CTT GTG GTG CTG GTG GGC GCG CTT GGA    1463
Pro Thr Gly Pro Ala Pro Trp Leu Val Val Leu Val Gly Ala Leu Gly
            420                 425                 430

CTC GCG GGA CTG GTG GGC ATC GCA GCC CTC GCC GTT CGG GTG TGC GCG    1511
Leu Ala Gly Leu Val Gly Ile Ala Ala Leu Ala Val Arg Val Cys Ala
            435                 440                 445

CGC CGC GCA AGC CAG AAG CGC ACC TAC GAC ATC CTC AAC CCC TTC GGG    1559
Arg Arg Ala Ser Gln Lys Arg Thr Tyr Asp Ile Leu Asn Pro Phe Gly
450                 451                 460

CCC GTA TAC ACC AGC TTG CCG ACC AAC GAG CCG CTC GAC GTG GTG GTG    1607
Pro Val Tyr Thr Ser Leu Pro Thr Asn Glu Pro Leu Asp Val Val Val
465                 470                 475                 480

CCA GTT AGC GAC GAC GAA TTT TCC CTC GAC GAA GAC TCT TTT GCG GAT    1655
Pro Val Ser Asp Asp Glu Phe Ser Leu Asp Glu Asp Ser Phe Ala Asp
                485                 490                 495

GAC GAC AGC GAC GAT GAC GGG CCC GCT AGC AAC CCC CCT GCG GAT GCC    1703
Asp Asp Ser Asp Asp Asp Gly Pro Ala Ser Asn Pro Pro Ala Asp Ala
            500                 505                 510

TAC GAC CTC GCC GGC GCC CCA GAG CCA ACT AGC GGG TTT GCG CGA GCC    1751
Tyr Asp Leu Ala Gly Ala Pro Glu Pro Thr Ser Gly Phe Ala Arg Ala
            515                 520                 525

CCC GCC AAC GGC ACG CGC TCG AGT CGC TCT GGG TTC AAA GTT TGG TTT    1799
Pro Ala Asn Gly Thr Arg Ser Ser Arg Ser Gly Phe Lys Val Trp Phe
            530                 535                 540

AGG GAC CCG CTT GAA GAC GAT GCC GCG CCA GCG CGG ACC CCG GCC GCA    1847
Arg Asp Pro Leu Glu Asp Asp Ala Ala Pro Ala Arg Thr Pro Ala Ala
545                 550                 555                 560

CCA GAT TAC ACC GTG GTA GCA GCG CGA CTC AAG TCC ATC CTC CGC TAG    1895
Pro Asp Tyr Thr Val Val Ala Ala Arg Leu Lys Ser Ile Leu Arg  *
                565                 570                 575

GCGCCCCCCC CCCCCCGCGC GCTGTGCCGT CTGACGGAAA GCACCCGCGT             1945

GTAGGGCTGC ATATAAATGG AGCGCTCACA CAAAGCCTCG TGCGGCTGCT             1995

TCGAAGGCAT GGAGAGTCCA CGCAGCGTCG TC                                2027

(2) INFORMATION FOR SEQ ID NO:2:

(i) SEQUENCE CHARACTERISTICS:
        (A) LENGTH: 284 nucleotides
        (B) TYPE: nucleotide
        (C) STRANDEDNESS: single
        (D) TOPOLOGY: Linear (xi) SEQUENCE DESCRIPTION: SEQ ID NO:2:

CTA CCA CGC CGC GGG CGA CTG CTT CGT TAT GCT GCA GAC GAC CGC GTT    48
Tyr His Ala Ala Gly Ala Cys Phe Val Met Leu Gln Thr Thr Ala Phe
                5                   10                  15

CGC CTC CTG CCC GCG CGT CGC GAA CGA CGC CTT TCG CTC CTG CCT GCA    96
Ala Ser Cys Pro Arg Val Ala Asn Asp Ala Phe Arg Ser Cys Leu His
            20                  25                  30

CGC CGA CAC GCG CCC CGC TCG CAG CGA GCG GCG CGC GAG CGC CGC GGT    144
Ala Asp Thr Arg Pro Ala Arg Ser Gln Arg Ala Ala Arg Ser Ala Ala Val
            35                  40                  45

CGA AAA CCA CGT GCT CTT CTC CAT CGC CCA TCC GCG CCC AAT AGA CTC    192
Glu Asn His Val Leu Phe Ser Ile Ala His Pro Arg Pro Ile Asp Ser
50                  55                  60
```

```
AGG GCT CTA CTT TCT GCG CGT CGG CAT CTA C GG CGG CAC CGC GGG CAG      240
Gly Leu Tyr Phe Leu Arg Val Gly Ile Tyr G ly Gly Thr Ala Gly Ser
 65                  70                  75                  80

CGA GCG CCG CCG AGA CGT CTT TCC CTT GGC C GC GTT TGT ACA CA           284
Glu Arg Arg Arg Asp Val Phe Pro Leu Ala A la Phe Val His
                     85                  90
```

(2) INFORMATION FOR SEQ ID NO:3:

(i) SEQUENCE CHARACTERISTICS:
        (A) LENGTH: 97 amino acids
        (B) TYPE: amino acid
        (C) STRANDEDNESS: single
        (D) TOPOLOGY: Linear (xi) SEQUENCE DESCRIPTION: SEQ ID NO :3:

```
Tyr His Ala Ala Gly Asp Xaa Cys Phe Val M et Leu Gln Thr Thr Ala
                 5                  10                  15

Phe Ala Ser Cys Pro Arg Val Ala Asn Xaa A la Phe Arg Ser Cys Leu
                20                  25                  30

His Ala Asp Thr Arg Pro Xaa Ala Arg Ser G lu Arg Arg Ala Ser Ala
            35                  40                  45

Ala Val Glu Asn His Val Leu Phe Ser Ile A la His Pro Arg Pro Ile
     50                  55                  60

Asp Ser Gly Leu Tyr Phe Leu Arg Val Gly I le Tyr Gly Gly Xaa Thr
 65                  70                  75                  80

Ala Gly Ser Glu Arg Arg Arg Asp Val Phe P ro Leu Ala Ala Phe Val
                 85                  90                  95

His
```

(2) INFORMATION FOR SEQ ID NO:4:

(i) SEQUENCE CHARACTERISTICS:
        (A) LENGTH: 98 amino acids
        (B) TYPE: amino acid
        (C) STRANDEDNESS: single
        (D) TOPOLOGY: Linear (xi) SEQUENCE DESCRIPTION: SEQ ID NO :4:

```
Arg Leu Asp Pro Lys Arg Ala Xaa Cys Tyr T hr Arg Glu Tyr Ala Ala
                 5                  10                  15

Glu Tyr Asp Leu Cys Pro Arg Val His His G lu Ala Phe Arg Gly Cys
                20                  25                  30

Leu Arg Xaa Xaa Xaa Lys Arg Xaa Glu Pro L eu Ala Arg Arg Ala Ser
            35                  40                  45

Ala Ala Val Glu Ala Arg Arg Leu Leu Phe V al Ser Arg Pro Ala Pro
     50                  55                  60

Pro Asp Ala Gly Ser Tyr Val Leu Arg Val A rg Xaa Xaa Asn Gly Xaa
 65                  70                  75                  80

Thr Thr Asp Leu Phe Val Leu Thr Ala Leu V al Pro Pro Arg Gly Arg
                 85                  90                  95

Pro His
```

(2) INFORMATION FOR SEQ ID NO:5:

(i) SEQUENCE CHARACTERISTICS:
        (A) LENGTH: 94 amino acids
        (B) TYPE: amino acid
        (C) STRANDEDNESS: single
        (D) TOPOLOGY: Linear (xi) SEQUENCE DESCRIPTION: SEQ ID NO:5:

Tyr Pro Met Gly His Lys Xaa Cys Pro Arg Val Val His Val Val Thr
                  5                  10                 15

Val Thr Ala Cys Pro Arg Arg Pro Ala Val Ala Phe Ala Leu Cys Arg
             20                  25                 30

Ala Thr Asp Ser Thr His Xaa Ser Pro Ala Tyr Pro Thr Leu Glu Leu
             35                  40                 45

Asn Leu Ala Gln Gln Pro Leu Leu Arg Val Gln Arg Ala Thr Arg Asp
         50                  55                 60

Tyr Ala Gly Val Tyr Val Leu Arg Val Trp Val Gly Asp Ala Pro Asn
 65              70                  75                  80

Ala Ser Leu Phe Val Leu Gly Met Ala Ile Ala Ala Glu Gly
                 85                  90

(2) INFORMATION FOR SEQ ID NO:6:

(i) SEQUENCE CHARACTERISTICS:
        (A) LENGTH: 94 amino acids
        (B) TYPE: amino acid
        (C) STRANDEDNESS: single
        (D) TOPOLOGY: Linear (xi) SEQUENCE DESCRIPTION: SEQ ID NO:6:

Tyr Ala Asp Thr Val Ala Phe Cys Phe Arg Ser Val Gln Val Ile Arg
                  5                  10                 15

Tyr Asp Gly Cys Pro Arg Ile Arg Thr Ser Ala Phe Ile Ser Cys Arg
             20                  25                 30

Tyr Lys His Ser Trp His Tyr Gly Asn Ser Thr Asp Arg Ile Ser Thr
             35                  40                 45

Glu Pro Asp Ala Gly Val Met Leu Lys Ile Thr Lys Pro Gly Ile Asn
         50                  55                 60

Asp Ala Gly Val Tyr Val Leu Leu Val Arg Leu Asp His Ser Arg Ser
 65              70                  75                  80

Thr Asp Gly Phe Ile Leu Gly Val Asn Val Tyr Thr Ala Gly
                 85                  90

(2) INFORMATION FOR SEQ ID NO:7:

(i) SEQUENCE CHARACTERISTICS:
        (A) LENGTH: 155 amino acids
        (B) TYPE: amino acid
        (C) STRANDEDNESS: single
        (D) TOPOLOGY: Linear (xi) SEQUENCE DESCRIPTION: SEQ ID NO:7:

His Ser Gln Leu Phe Ser Pro Gly Asp Thr Phe Asp Leu Met Pro Arg
                  5                  10                 15

Val Val Ser Asp Met Gly Asp Ser Arg Glu Asn Thr Phe Thr Ala Thr
             20                  25                 30

Leu Asp Trp Tyr Tyr Ala Arg Ala Pro Pro Arg Cys Leu Leu Tyr Tyr
             35                  40                 45

Val Tyr Glu Pro Cys Ile Tyr His Pro Arg Ala Pro Glu Cys Leu Arg
         50                  55                 60

Pro Val Asp Pro Ala Cys Ser Phe Thr Ser Pro Ala Arg Ala Ala Leu
 65              70                  75                  80

Val Ala Arg Arg Ala Tyr Ala Ser Cys Ser Pro Leu Leu Gly Asp Arg
                 85                  90                 95

```
Trp Leu Thr Ala Cys Pro Phe Asp Ala Phe Gly Glu Glu Val His Xaa
                100                 105                 110

Xaa Xaa Xaa Xaa Xaa Xaa Xaa Xaa Xaa Xaa Xaa Thr Asn Ala Thr
        115                 120                 125

Ala Asp Glu Ser Gly Leu Tyr Val Leu Val Met Thr His Asn Gly His
    130                 135                 140

Val Ala Thr Trp Asp Tyr Thr Leu Val Ala Thr
145                 150                 155
```

(2) INFORMATION FOR SEQ ID NO:8:

(i) SEQUENCE CHARACTERISTICS:
        (A) LENGTH: 155 amino acids
        (B) TYPE: amino acid
        (C) STRANDEDNESS: single
        (D) TOPOLOGY: Linear (xi) SEQUENCE DESCRIPTION: SEQ ID NO:8:

```
His Ser His Val Phe Ser Val Gly Asp Thr Phe Ser Leu Ala Met His
                5                   10                  15

Leu Gln Tyr Lys Ile Xaa His Xaa Xaa Glu Ala Pro Phe Asp Leu Leu
            20                  25                  30

Leu Glu Trp Leu Tyr Val Pro Ile Asp Pro Thr Cys Gln Pro Met Arg
        35                  40                  45

Leu Tyr Ser Thr Cys Leu Tyr His Pro Asn Ala Pro Gln Cys Leu Ser
    50                  55                  60

His Met Asn Ser Gly Cys Thr Phe Thr Ser Pro His Leu Ala Gln Arg
65                  70                  75                  80

Val Ala Ser Thr Val Tyr Gln Asn Cys Xaa Xaa Glu His Ala Asp Asn
                85                  90                  95

Tyr Thr Ala Tyr Cys Leu Gly Ile Ser His Met Glu Pro Ser Phe Gly
                100                 105                 110

Leu Ile Leu His Asp Gly Gly Thr Thr Leu Lys Phe Val Asp Thr Pro
            115                 120                 125

Glu Ser Leu Ser Gly Leu Tyr Val Phe Tyr Val Tyr Phe Asn Gly His
    130                 135                 140

Val Glu Ala Val Ala Tyr Thr Val Val Ser Thr
145                 150                 155
```

(2) INFORMATION FOR SEQ ID NO:9:

(i) SEQUENCE CHARACTERISTICS:
        (A) LENGTH: 155 amino acids
        (B) TYPE: amino acid
        (C) STRANDEDNESS: single
        (D) TOPOLOGY: Linear (xi) SEQUENCE DESCRIPTION: SEQ ID NO:9:

```
His Ser His Val Tyr Thr Pro Gly Asp Ser Phe Leu Leu Ser Val Arg
                5                   10                  15

Leu Gln Ser Glu Phe Phe Asp Xaa Xaa Glu Ala Pro Phe Ser Ala Ser
            20                  25                  30

Ile Asp Trp Tyr Phe Leu Arg Thr Ala Gly Asp Cys Ala Leu Ile Arg
        35                  40                  45

Ile Tyr Glu Thr Cys Ile Phe His Pro Glu Ala Pro Ala Cys Leu His
    50                  55                  60

Pro Ala Asp Ala Gln Cys Thr Phe Ala Ser Pro Tyr Arg Ser Glu Thr
65                  70                  75                  80
```

```
Val Tyr Ser Arg Leu Tyr Glu Gln Cys Arg Pro Asp Pro Ala Gly Arg
                85                  90                  95

Trp Pro His Glu Cys Glu Gly Ala Ala Tyr Ala Ala Pro Val Ala His
            100                 105                 110

Leu Arg Pro Ala Asn Asn Ser Val Asp Leu Val Phe Asp Asp Ala Pro
        115                 120                 125

Ala Ala Ala Ser Gly Leu Tyr Val Phe Val Leu Gln Tyr Asn Gly His
    130                 135                 140

Val Glu Ala Trp Asp Tyr Ser Leu Val Val Thr
145                 150                 155
```

(2) INFORMATION FOR SEQ ID NO:10:

(i) SEQUENCE CHARACTERISTICS:
        (A) LENGTH: 155 amino acids
        (B) TYPE: amino acid
        (C) STRANDEDNESS: single
        (D) TOPOLOGY: Linear (xi) SEQUENCE DESCRIPTION: SEQ ID NO:10:

```
Glu Ala Ile Leu Phe Ser Pro Gly Glu Thr Phe Ser Thr Asn Val Ser
                 5                  10                  15

Ile His Ala Ile Ala His Asp Xaa Xaa Asp Gln Thr Tyr Ser Met Asp
            20                  25                  30

Val Val Trp Leu Arg Phe Asp Val Pro Thr Ser Cys Ala Glu Met Arg
        35                  40                  45

Ile Tyr Glu Ser Cys Leu Tyr His Pro Gln Leu Pro Glu Cys Leu Ser
    50                  55                  60

Pro Ala Asp Ala Pro Cys Xaa Xaa Ala Ala Ser Thr Trp Thr Ser Arg
65                  70                  75                  80

Leu Ala Val Arg Ser Tyr Ala Gly Cys Ser Arg Thr Asn Pro Xaa Xaa
                85                  90                  95

Xaa Pro Pro Arg Cys Ser Ala Glu Ala His Met Glu Pro Val Pro Gly
            100                 105                 110

Leu Ala Trp Gln Ala Ala Ser Val Asn Leu Glu Phe Arg Asp Ala Ser
        115                 120                 125

Pro Gln His Ser Gly Leu Tyr Leu Cys Val Val Tyr Val Asn Asp His
    130                 135                 140

Ile His Ala Trp Gly His Ile Thr Ile Ser Thr
145                 150                 155
```

(2) INFORMATION FOR SEQ ID NO:11:

(i) SEQUENCE CHARACTERISTICS:
        (A) LENGTH: 208 nucleotides
        (B) TYPE: nucleotide
        (C) STRANDEDNESS: single
        (D) TOPOLOGY: Linear (xi) SEQUENCE DESCRIPTION: SEQ ID NO:11:

```
GAGCGGCCCG ACCGCCGCCG GGTTGTTAAA TGGGTCTCGC GCGGCTCGTG            50

GTTCCACACC GCCGGAGAAC CAGCGCTGCG AGGGGGGGCT TGGTGGCTGG           100

CGACTCTTTA AGGCGTGCCG CCACGAGCAA GAAGACGGCC TGTATGCTAT           150

GCTCCCGCCG GACTATTTTC CGGTGGTGCC CTCGTCCAAG CCCCTGCTGG           200

TGAAAGTT                                                         208
```

(2) INFORMATION FOR SEQ ID NO:12:

(i) SEQUENCE CHARACTERISTICS:
    (A) LENGTH: 64 nuc leotides
    (B) TYPE: nucleotide
    (C) STRANDEDNESS: sin gle
    (D) TOPOLOGY: Linear (xi) SEQUENCE DESCRIPTION: SEQ ID NO :12:

```
GGCACCGGTC CCGGATGCGA GGGGGGGCTT GGCCGGAGAA CCAGCGCTGC          50

GAGGGGGGGC TTGG                                                 64
```

(2) INFORMATION FOR SEQ ID NO:13:

(i) SEQUENCE CHARACTERISTICS:
        (A) LENGTH: 64 nuc leotides
        (B) TYPE: nucleotide
        (C) STRANDEDNESS: sin gle
        (D) TOPOLOGY: Linear (xi) SEQUENCE DESCRIPTION: SEQ ID NO :13:

```
CCGGAGAACC AGCGCTGCGA GGGGGGGCTT GGCCGGAGAA CCAGCGCGAG          50

CTTCGCTGCG TGTG                                                 64
```

(2) INFORMATION FOR SEQ ID NO:14:

(i) SEQUENCE CHARACTERISTICS:
        (A) LENGTH: 756 nu cleotides
        (B) TYPE: nucleotide
        (C) STRANDEDNESS: sin gle
        (D) TOPOLOGY: Linear (xi) SEQUENCE DESCRIPTION: SEQ ID NO :14:

```
GGCCACGTGG AAGCTTGGGA CTACAGCCTA GTCGTTACTT CGGACCGTTT          50

GGTGCGCGCG GTCACCGACC ACACGCGCCC CGAGGCCGCA GCCGCCGACG         100

CTCCCGAGCC AGGCCCACCG CTCACCAGCG AGCCGGCGGG CGCGCCCACC         150

GGGCCCGCGC CCTGGCTTGT GGTGCTGGTG GGCGCGCTTG GACTCGCGGG         200

ACTGGTGGGC ATCGCAGCCC TCGCCGTTCG GGTGTGCGCG CGCCGCGCAA         250

GCCAGAAGCG CACCTACGAC ATCCTCAACC CCTTCGGGCC CGTATACACC         300

AGCTTGCCGA CCAACGAGCC GCTCGACGTG GTGGTGCCAG TTAGCGACGA         350

CGAATTTTCC CTCGACGAAG ACTCTTTTGC GGATGACGAC AGCGACGATG         400

ACGGGCCCGC TAGCAACCCC CCTGCGGATG CCTACGACCT CGCCGGCGCC         450

CCAGAGCCAA CTAGCGGGTT TGCGCGAGCC CCCGCCAACG GCACGCGCTC         500

GAGTCGCTCT GGGTTCAAAG TTTGGTTTAG GGACCCGCTT GAAGACGATG         550

CCGCGCCAGC GCGGACCCCG GCCGCACCAG ATTACACCGT GGTAGCAGCG         600

CGACTCAAGT CCATCCTCCG CTAGGCGCCC CCCCCCCCC GCGCGCTGTG          650

CCGTCTGACG GAAAGCACCC GCGTGTAGGG CTGCATATAA ATGGAGCGCT         700

CACACAAAGC CTCGTGCGGC TGCTTCGAAG GCATGGAGAG TCCACGCAGC         750

GTCGTC                                                         756
```

(2) INFORMATION FOR SEQ ID NO:15:

(i) SEQUENCE CHARACTERISTICS:
        (A) LENGTH: 20 nuc leotides
        (B) TYPE: nucleotide
        (C) STRANDEDNESS: sin gle
        (D) TOPOLOGY: Linear -continued (xi) SEQUENCE DESCRIPTION: SEQ ID NO :15:

ACGTGGTGGT GCCAGTTAGC                                                                          20

(2) INFORMATION FOR SEQ ID NO:16:

(i) SEQUENCE CHARACTERISTICS:
        (A) LENGTH:  22 nuc leotides
        (B) TYPE:  nucleotide
        (C) STRANDEDNESS:  sin gle
        (D) TOPOLOGY:  Linear (xi) SEQUENCE DESCRIPTION: SEQ ID NO :16:

ACCAAACTTT GAACCCAGAG CG                                                                       22